US012624031B2

(12) United States Patent
Fang et al.

(10) Patent No.: US 12,624,031 B2
(45) Date of Patent: May 12, 2026

(54) INHIBITORS OF UBIQUITIN SPECIFIC PEPTIDASE 22 (USP22) AND USES THEREOF FOR TREATING DISEASES AND DISORDERS

(71) Applicant: Northwestern University, Evanston, IL (US)

(72) Inventors: Deyu Fang, Evanston, IL (US); Amy Tang, Evanston, IL (US); Beixue Gao, Evanston, IL (US); Elena Montauti, Evanston, IL (US); Ming Yan, Evanston, IL (US); Huiping Liu, Evanston, IL (US)

(73) Assignee: Northwestern University, Evanston, IL (US)

( * ) Notice: Subject to any disclaimer, the term of this patent is extended or adjusted under 35 U.S.C. 154(b) by 477 days.

(21) Appl. No.: 18/306,978

(22) Filed: Apr. 25, 2023

(65) Prior Publication Data

US 2023/0339942 A1 Oct. 26, 2023

Related U.S. Application Data

(60) Provisional application No. 63/334,454, filed on Apr. 25, 2022.

(51) Int. Cl.
*C07D 471/04* (2006.01)
*A61P 35/00* (2006.01)

(52) U.S. Cl.
CPC ............ *C07D 471/04* (2013.01); *A61P 35/00* (2018.01)

(58) Field of Classification Search
CPC .................................................... C07D 471/04
USPC .......................................................... 514/300
See application file for complete search history.

(56) References Cited

U.S. PATENT DOCUMENTS

2024/0238274 A1 7/2024 Fang et al.

FOREIGN PATENT DOCUMENTS

WO 2022226402 * 10/2022

OTHER PUBLICATIONS

E. Montauti, S.E. Weinberg, P. Chu, S. Chaudhuri, N.L. Mani, R. Iyer, Y. Zhou, Y. Zhang, C. Liu, C. Xin, S. Gregory, J. Wei, Y. Zhang, W. Chen, Z. Sun, M. Yan, D. Fang, A deubiquitination module essential for T(reg) fitness in the tumor microenvironment, Sci Adv 8 (2022) eabo4116. 10.1126/sciadv.abo4116.

N.L. Samara, A.B. Datta, C.E. Berndsen, X. Zhang, T. Yao, R.E. Cohen, C. Wolberger, Structural insights into the assembly and function of the SAGA deubiquitinating module, Science 328 (2010) 1025-1029. 10.1126/science.1190049.

A.. Kohler, E. Zimmerman, M. Schneider, E. Hurt, N. Zheng, Structural basis for assembly and activation of the heterotetrameric SAGA histone H2B deubiquitinase module, Cell 141 (2010) 606-617. 10.1016/j.cell.2010.04.026.

Z. Lin, H. Yang, Q. Kong, J. Li, S.-M. Lee, B. Gao, H. Dong, J. Wei, J. Song, D.D. Zhang, D. Fang, USP22 Antagonizes p53 Transcriptional Activation by Deubiquitinating Sirt1 to Suppress Cell Apoptosis and Is Required for Mouse Embryonic Development, Molecular Cell 46 (2012) 484-494. 10.1016/j.molcel.2012.03.024.

M. Morgan, T. Ikenoue, H. Suga, C. Wolberger, Potent macrocycle inhibitors of the human SAGA deubiquitinating module, Cell Chem Biol 29 (2022) 544-554 e544. 10.1016/j.chembiol.2021.12.004.

X. Huang, Q. Zhang, Y. Lou, J. Wang, X. Zhao, L. Wang, X. Zhang, S. Li, Y. Zhao, Q. Chen, T. Liang, X. Bai, USP22 Deubiquitinates CD274 to Suppress Anticancer Immunity, Cancer Immunol Res 7 (2019) 1580-1590. 10.1158/2326-6066.CIR-18-0910.

S. Gregory, Y. Xu, P. Xie, J. Fan, B. Gao, N. Mani, R. Iyer, A. Tang, J. Wei, S.M. Chaudhuri, S. Wang, H. Liu, B. Zhang, D. Fang, The ubiquitin-specific peptidase 22 is a deubiquitinase of CD73 in breast cancer cells, Am J Cancer Res 12 (2022) 5564-5575.

* cited by examiner

*Primary Examiner* — Niloofar Rahmani
(74) *Attorney, Agent, or Firm* — Quarles & Brady LLP

(57) ABSTRACT

Disclosed are methods of treating diseases or disorders associated with the expression of Ubiquitin Specific Peptidase 22 (USP22). The disclosed methods may be utilized to treat diseases or disorders associated with cell proliferation, including cancer. Also disclosed are inhibitors of USP22 that specifically inhibit the EC:3.4.19.12 activity, or the thiol-dependent hydrolysis of ester, thioester, amide, peptide and isopeptide bonds formed by the C-terminal glycine of ubiquitin. The disclosed compounds may also be used in pharmaceutical compositions and methods for treatment of cell proliferative diseases or disorders associated with USP22 activity.

12 Claims, 30 Drawing Sheets

Specification includes a Sequence Listing.

| | IUPAC Nomenclature | Chemical Structure | Cyto-toxicity | FoxP3 Expression | PDL1 Expression |
|---|---|---|---|---|---|
| S100 | 11-chloro-7,8,9,10-tetrahydrobenzo[4,5]imidazo[1,2-*b*]isoquinoline-6-carbonitrile |  | N/A | N/A | N/A |
| S101 | 11-(phenylamino)-7,8,9,10-tetrahydrobenzo[4,5]imidazo[1,2-*b*]isoquinoline-6-carbonitrile |  | N/A | N/A | N/A |

| | IUPAC Nomenclature | Chemical Structure | Cyto-toxicity | FoxP3 Expression | PDL1 Expression |
|---|---|---|---|---|---|
| S102 | 11-((4-fluorophenyl)amino)-7,8,9,10-tetrahydrobenzo[4,5]imidazo[1,2-*b*]isoquinoline-6-carbonitrile |  | ++ | N/A | N/A |
| S103 | 11-((4-chlorophenyl)amino)-7,8,9,10-tetrahydrobenzo[4,5]imidazo[1,2-b]isoquinoline-6-carbonitrile |  | N/A | N/A | N/A |

| | IUPAC Nomenclature | Chemical Structure | Cyto-toxicity | FoxP3 Expression | PDL1 Expression |
|---|---|---|---|---|---|
| S104 | 11-((4-bromophenyl)amino)--7,8,9,10-tetrahydrobenzo[4,5]imidazo[1,2-*b*]isoquinoline-6-carbonitrile |  | + | N/A | N/A |
| S105 | 11-((4-(trifluoromethyl)phenyl)amino)-7,8,9,10-tetrahydrobenzo[4,5]imidazo[1,2-b]isoquinoline-6-carbonitrile |  | ++ | N/A | N/A |

| | IUPAC Nomenclature | Chemical Structure | Cyto-toxicity | FoxP3 Expression | PDL1 Expression |
|---|---|---|---|---|---|
| S106 | 11-((4-cyanophenyl)amino)-7,8,9,10-tetrahydrobenzo[4,5]imidazo[1,2-*b*]isoquinoline-6-carbonitrile |  | - | - | +/- |
| S107 | 11-((4-methoxyphenyl)amino)-7,8,9,10-tetrahydrobenzo[4,5]imidazo[1,2-*b*]isoquinoline-6-carbonitrile |  | - | + | +/- |

| | IUPAC Nomenclature | Chemical Structure | Cyto-toxicity | FoxP3 Expression | PDL1 Expression |
|---|---|---|---|---|---|
| S108 | 11-((4-nitrophenyl)amino)-7,8,9,10-tetrahydrobenzo[4,5]imidazo[1,2-*b*]isoquinoline-6-carbonitrile |  | N/A | N/A | N/A |
| S109 | 11-((4-isopropoxyphenyl)amino)-7,8,9,10-tetrahydrobenzo[4,5]imidazo[1,2-*b*]isoquinoline-6-carbonitrile |  | + | N/A | N/A |

| | IUPAC Nomenclature | Chemical Structure | Cyto-toxicity | FoxP3 Expression | PDL1 Expression |
|---|---|---|---|---|---|
| S110 | 4-((6-cyano-7,8,9,10-tetrahydrobenzo[4,5]imidazo[1,2-*b*]isoquinolin-11-yl)amino)benzoic acid |  | - | - | +/- |
| S111 | 11-((4-aminophenyl)amino)-7,8,9,10-tetrahydrobenzo[4,5]imidazo[1,2-*b*]isoquinoline-6-carbonitrile |  | + | N/A | N/A |

| | IUPAC Nomenclature | Chemical Structure | Cyto-toxicity | FoxP3 Expression | PDL1 Expression |
|---|---|---|---|---|---|
| S112 | 11-((4-(aminomethyl)phenyl)amino)-7,8,9,10-tetrahydrobenzo[4,5]imidazo[1,2-*b*]isoquinoline-6-carbonitrile |  | + | N/A | N/A |
| S113 | 11-((4-(methylamino)phenyl)amino)-7,8,9,10-tetrahydrobenzo[4,5]imidazo[1,2-*b*]isoquinoline-6-carbonitrile |  | + | N/A | N/A |

| | IUPAC Nomenclature | Chemical Structure | Cyto-toxicity | FoxP3 Expression | PDL1 Expression |
|---|---|---|---|---|---|
| S200 | 11-chloro-5-methyl-6,11-dihydro-5H-indolo[2,3-b]quinoline |  | N/A | N/A | N/A |
| S201 | N5-methyl-*N*-phenyl-5*H*-indolo[2,3-*b*]quinolin-11-amine |  | +++ | N/A | N/A |

| | IUPAC Nomenclature | Chemical Structure | Cyto-toxicity | FoxP3 Expression | PDL1 Expression |
|---|---|---|---|---|---|
| S202 | N,5-dimethyl-5H-indolo[2,3-b]quinolin-11-amine |  | +++ | N/A | N/A |

D
Usp22i-S02
WT
22KO
- + - +
FOXP3
USP22
p84
G
DMSO
Usp22i-S02
  ns
Foxp3 MFI
4000
3000
2000
1000
0
WT
21KO
22KO
I
Usp22i-S02
IP:Ub
IB:Foxp3
Input
IgG
Ub
0 0 5 10 15 20
Ub-Foxp3
Mono-Ub-Foxp3
Foxp3
J
Usp22i-S02
IP: Foxp3
IB: Ub
Input
IgG
Foxp3
0 0 5 10 15 20
Ub-Foxp3
Foxp3

S02 -300kJ/mol

S01 -342kJ/mol

S02

S02-X

A 1a 1b 1c

S100

S101 $R_1$ = H
S102 $R_1$ = F
S103 $R_1$ = Cl
S104 $R_1$ = Br
S105 $R_1$ = $CF_3$
S106 $R_1$ = CN
S107 $R_1$ = $OCH_3$

S108 $R_1$ = $NO_2$
S109 $R_1$ = $OCH(CH_3)_2$
S110 $R_1$ = COOH
S111 $R_1$ = $NH_2$
S112 $R_1$ = $CNH_2$
S113 $R_1$ = $NHCH_3$
S115 R1=-H, R2=-Cl, R3=-Cl
S116 R1=-Cl, R2=-Cl,R3=-Cl

Reagents and conditions:
(i) $NH_4OAc$, 140-150 °C, 4h;
(ii) $POCl_3$, reflux, 120 °C, 6h;
(iii) DMF, 120 °C, 6h.

B 2a 2b 2c 2d

S200 S201-S202

S201 R=-H
S202 R=-OMe

Reagents and conditions:
(i) NCS,1,4-dimethylpiperazine, DCM, trichloroacetic acid;
(ii) diphenyl ether, reflux;
(iii) POCl3, toluene, reflux;
(iv) DMF, Aniline or p-Anisidine, 120 °C.

A

B

C

| Compounds | IC50 (μM) |
|---|---|
| S02 | 4.7 |
| S02-S100 | NA |
| S02-S101 | NA |
| S02-S102 | 17.2 |
| S02-S103 | NA |
| S02-S104 | 13.9 |
| S02-S105 | **2.8** |
| S02-S106 | **0.6** |
| S02-S107 | **3.3** |
| S02-S108 | NA |
| S02-S109 | 19.3 |
| S02-S110 | 22.8 |
| S02-S111 | NA |
| S02-S112 | >20 |
| S02-S113 | **0.3** |
| S02-S200 | >20 |
| S02-S201 | NA |
| S02-S202 | 11.2 |

SEQUENCE LISTING

```
Sequence total quantity: 2
SEQ ID NO: 1            moltype = AA  length = 525
FEATURE                 Location/Qualifiers
source                  1..525
                        mol_type = protein
```

-continued

```
                         organism = Homo sapiens
SEQUENCE: 1
MVSRPEPEGE AMDAELAVAP PGCSHLGSFK VDNWKQNLRA IYQCFVWSGT AEARKRKAKS  60
CICHVCGVHL NRLHSCLYCV FFGCFTKKHI HEHAKAKRHN LAIDLMYGGI YCFLCQDYIY  120
DKDMEIIAKE EQRKAWKMQG VGEKFSTWEP TKRELELLKH NPKRRKITSN CTIGLRGLIN  180
LGNTCFMNCI VQALTHTPLL RDFFLSDRHR CEMQSPSSCL VCEMSSLFQE FYSGHRSPHI  240
PYKLLHLVWT HARHLAGYEQ QDAHEFLIAA LDVLHRHCKG DDNGKKANNP NHCNCIIDQI  300
FTGGLQSDVT CQVCHGVSTT IDPFWDISLD LPGSSTPFWP LSPGSEGNVV NGESHVSGTT  360
TLTDCLRRFT RPEHLGSSAK IKCSGCHSYQ ESTKQLTMKK LPIVACFHLK RFEHSAKLRR  420
KITTYVSFPL ELDMTPFMAS SKESRMNGQY QQPTDSLNND NKYSLFAVVN HQGTLESGHY  480
TSFIRQHKDQ WFKCDDAIIT KASIKDVLDS EGYLLFYHKQ FLEYE                525

SEQ ID NO: 2             moltype = AA  length = 513
FEATURE                  Location/Qualifiers
source                   1..513
                         mol_type = protein
                         organism = Homo sapiens
SEQUENCE: 2
MAPGWPSLSA GSRQEAPQLA AGGSAYQAVG RQFQPRATAL QGPSQAKSCI CHVCGVHLNR  60
LHSCLYCVFF GCFTKKHIHE HAKAKRHNLA IDLMYGGIYC FLCQDYIYDK DMEIIAKEEQ  120
RKAWKMQGVG EKFSTWEPTK RELELLKHNP KRRKITSNCT IGLRGLINLG NTCFMNCIVQ  180
ALTHTPLLRD FFLSDRHRCE MQSPSSCLVC EMSSLFQEFY SGHRSPHIPY KLLHLVWTHA  240
RHLAGYEQQD AHEFLIAALD VLHRHCKGDD NGKKANNPNH CNCIIDQIFT GGLQSDVTCQ  300
VCHGVSTTID PFWDISLDLP GSSTPFWPLS PGSEGNVVNG ESHVSGTTTL TDCLRRFTRP  360
EHLGSSAKIK CSGCHSYQES TKQLTMKKLP IVACFHLKRF EHSAKLRRKI TTYVSFPLEL  420
DMTPFMASSK ESRMNGQYQQ PTDSLNNDNK YSLFAVVNHQ GTLESGHYTS FIRQHKDQWF  480
KCDDAIITKA SIKDVLDSEG YLLFYHKQFL EYE                             513
```

INHIBITORS OF UBIQUITIN SPECIFIC PEPTIDASE 22 (USP22) AND USES THEREOF FOR TREATING DISEASES AND DISORDERS

CROSS REFERENCE TO RELATED APPLICATIONS

The present application claims priority to U.S. Provisional Patent Application No. 63/334,454 that was filed Apr. 25, 2022, the entire contents of which are hereby incorporated by reference.

SEQUENCE LISTING

A Sequence Listing accompanies this application and is submitted as an xml file of the sequence listing named "702581_02253.xml" which is 3,701 bytes in size and was created on Apr. 19, 2023. The sequence listing is electronically submitted via Patent Center and is incorporated herein by reference in its entirety.

BACKGROUND OF THE INVENTION

The field of the invention relates to small molecule inhibitors of ubiquitin specific peptidase 22 (USP22) and the use thereof in treating diseases and disorders associated with USP22 biological activity. In particular, the field of the invention relates to small molecule inhibitors of the peptidase activity of USP22 which may be formulated as pharmaceutical compositions for treatment of immune deficiency, infectious diseases, and cell proliferative diseases and disorders such as cancer.

The expression of ubiquitin specific peptidase 22 (USP22) is often increased in many, if not all types of human cancers. USP22 functions as a potential oncogene in tumorigenesis and progression in lung and colon cancer in part through diminishing the tumor suppressor p53 transcriptional activity and promoting cell cycle progression. Mice with genetic USP22 suppression in immune cells have better tumor rejection using multiple syngeneic tumor models including lung cancer, lymphoma, melanoma, and colon cancers. These results indicate that USP22 is an ideal therapeutic target in antitumor therapy because that, on one hand, inhibition of USP22 in tumor cells can directly induces their apoptosis and blocks cell cycle progression, on the other hand, USP22 suppression in immune cells enhances immunity. In addition, USP22 inhibition can improve immune response to combat all pathogens in treatment of infectious diseases and immune deficient diseases.

SUMMARY OF THE INVENTION

In an aspect of the current disclosure, compounds are provided. In some embodiments, the compounds have the formula (Ia)

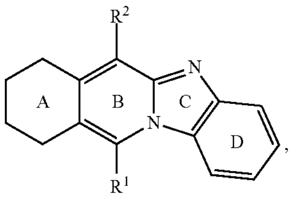

-continued (Ib)

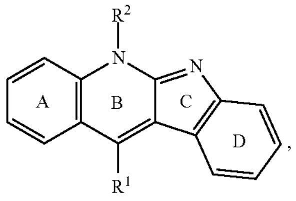

or (Ic)

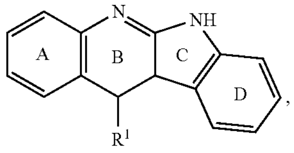

or a pharmaceutically acceptable salt thereof, where $R^2$ is selected from cyano and alkyl and $R^1$ is —NH-phenyl, the phenyl optionally substituted with halo, —CN, alkyl, alkoxy, —$NO_2$, amino, and —COOH and wherein the alkyl is optionally substituted with a halo or amino, or halo. In some embodiments, the compounds have the formula Ia. In some embodiments, the compounds have the formula Ib. In some embodiments, the compounds have the formula Ic.

In some embodiments, $R^2$ is selected from cyano and $R^1$ is —NH-phenyl, the phenyl substituted with halo, —CN, alkyl, alkoxy, —$NO_2$, amino, and —COOH and wherein the alkyl is optionally substituted with a halo or amino, or halo. In some embodiments, the compounds have the formula Ia. In some embodiments, the compounds have the formula Ib. In some embodiments, the compounds have the formula Ic.

In some embodiments, $R^2$ is selected from alkyl and $R^1$ is —NH-phenyl, the phenyl optionally substituted with halo, —CN, alkyl, alkoxy, —$NO_2$, amino, and —COOH and wherein the alkyl is optionally substituted with a halo or amino, or halo. In some embodiments, the compounds have the formula Ia. In some embodiments, the compounds have the formula Ib. In some embodiments, the compounds have the formula Ic.

In some embodiments, the compounds have the formula

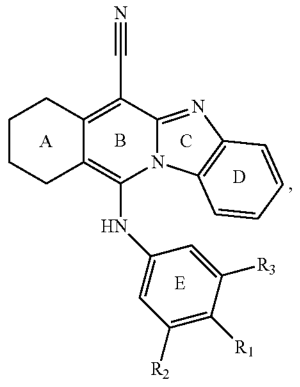

or a pharmaceutically acceptable salt thereof, where $R_1$, $R_2$, and $R_3$ are independently selected from hydrogen, halo, —CN, alkyl, alkoxy, —$NO_2$, amino, and —COOH, wherein the alkyl is optionally substituted with a halo or amino, and wherein $R_1$, $R_2$, and $R_3$ are not each hydrogen.

In some embodiments, the compounds are selected from
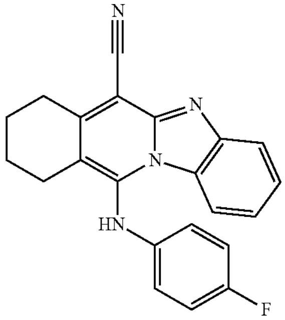
,
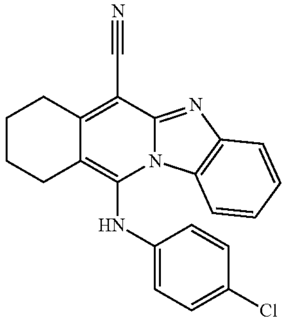
,
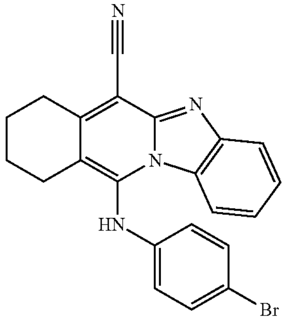
,
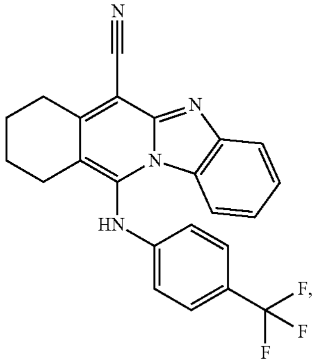
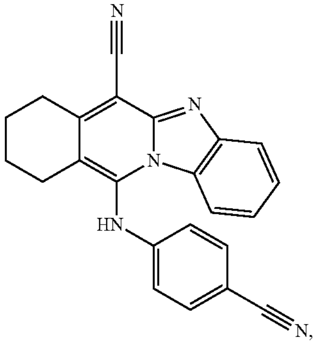
-continued
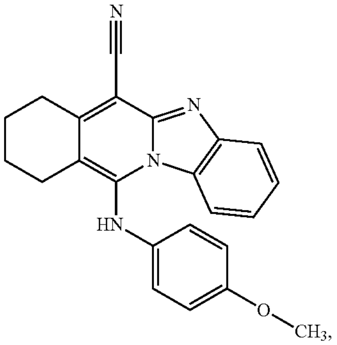
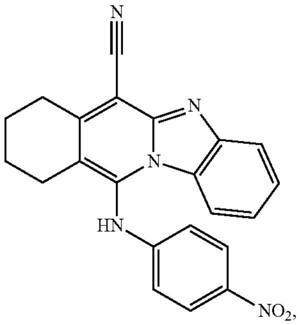
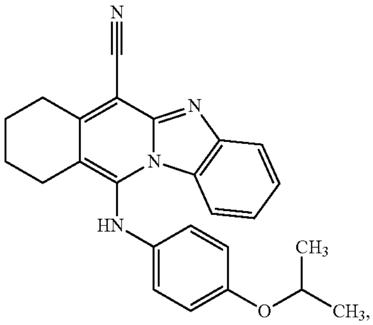
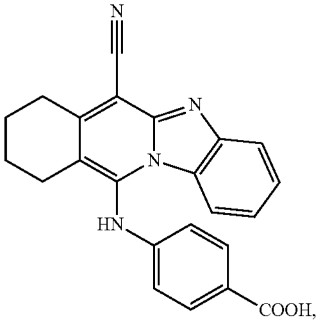
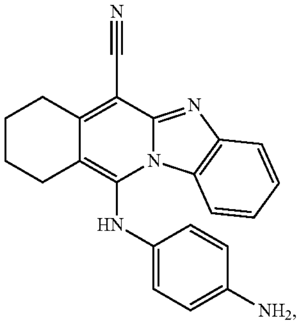

-continued
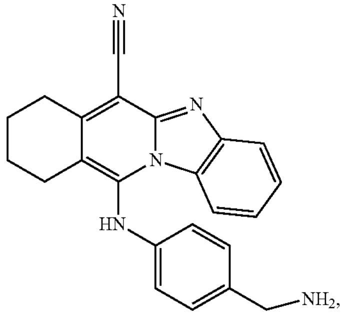
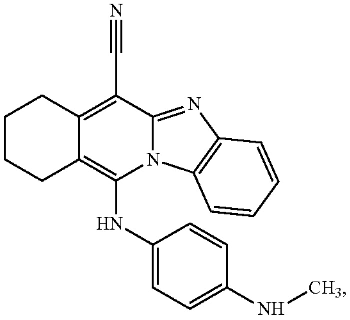
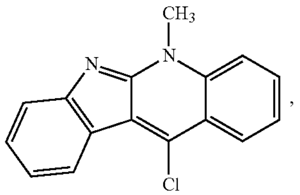
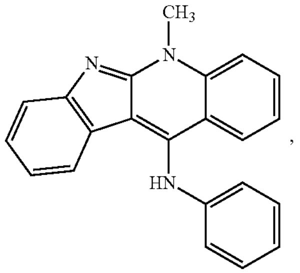
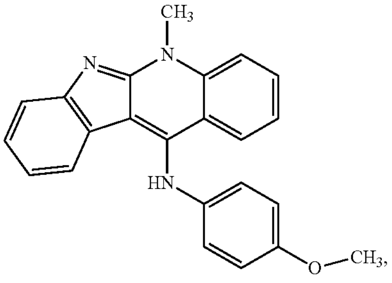
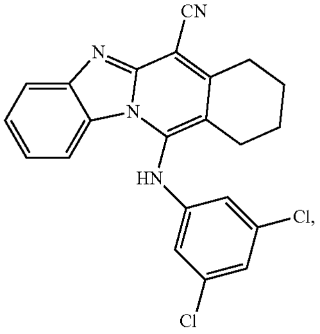
and
-continued
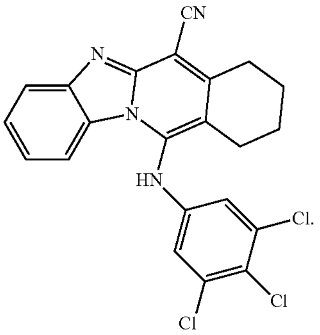
In some embodiments, the compound is
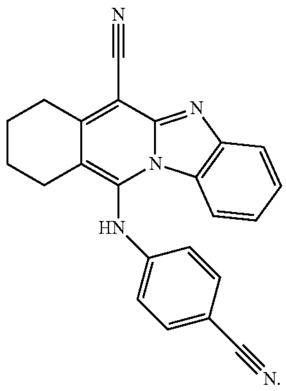 [SMILES: N#Cc1ccc(Nc2c3c(c(C#N)c4nc5ccccc5n24)CCCC3)cc1]
In some embodiments, the compound is
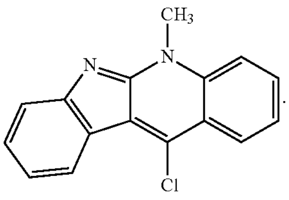 [SMILES: Cn1c2nc3ccccc3c-2c(Cl)c2ccccc21]
In some embodiments, the compound is selected from
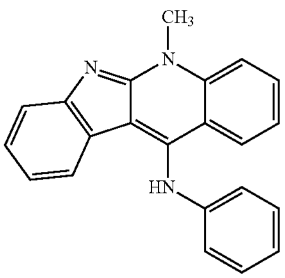
or -continued

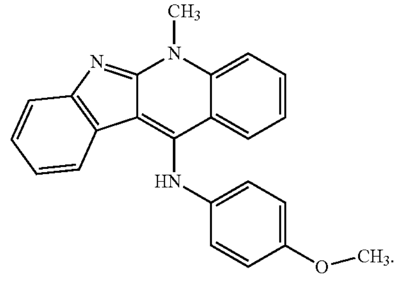

In another aspect of the current disclosure, pharmaceutical compositions are provided. In some embodiments, the pharmaceutical compositions comprise a compound, or a pharmaceutically acceptable salt thereof, and a pharmaceutically acceptable carrier, excipient, or diluent. In some embodiments, the composition comprises an effective amount of the compound for inhibiting biological activity of USP22 when administered to a subject in need thereof. In some embodiments, the composition comprises an effective amount of the compound for suppressing Treg cell activity in a subject in need thereof. In some embodiments, the composition comprises an effective amount of the compound for inhibiting ubiquitin specific peptidase activity (E.C. 3.4.19.12) of USP22 in a subject in need thereof.

In another aspect of the current disclosure, methods of treating a subject in need of treatment for a disease or disorder associated with ubiquitin specific peptidase 22 (USP22) activity are provided. In some embodiments, the methods comprise administering to the subject an effective amount of a pharmaceutical composition comprising a compound disclosed herein, or a pharmaceutically acceptable salt thereof. In some embodiments, the disease or disorder is a cell proliferative disease or disorder. In some embodiments, the disease or disorder is cancer. In some embodiments, the disease or disorder is a cancer selected from the group consisting of lung cancer, gastric carcinoma, pancreatic cancer, melanoma, lymphoma, colon cancer, breast cancer, ovarian cancer, bladder cancer, prostate cancer, glioma, mesothelioma, neuroblastoma, mantle cell lymphoma, and acute myeloid leukemia. In some embodiments, the disease or disorder is lung cancer. In some embodiments, the disease or disorder is melanoma.

In another aspect of the current disclosure, method of suppressing Treg cell activity in a subject in need thereof are provided. In some embodiments, the methods comprise administering to the subject an effective amount of a pharmaceutical composition comprising a compound disclosed herein, or a pharmaceutically acceptable salt thereof.

In another aspect of the current disclosure, methods for inhibiting ubiquitin specific peptidase activity (E.C. 3.4.19.12) of USP22 in a subject in need thereof are provided. In some embodiments, the methods comprise administering to the subject an effective amount of a pharmaceutical composition comprising a compound disclosed herein, or a pharmaceutically acceptable salt thereof.

BRIEF DESCRIPTION OF THE FIGURES

(FIG. 3) Representative histograms of FITC::FoxP3 MFI in nTregs cultured with inhibitors at a concentration of 2 μg/mL. (FIG. 4) Representative plot of FITC::FoxP3 geometric MFI in nTregs across different concentrations of inhibitor. Inhibitors [S106, S110] show higher efficacy compared to usp22i-s02 at a concentration of 2 μg/mL in decreasing FoxP3 expression.

DETAILED DESCRIPTION

Figure 1:
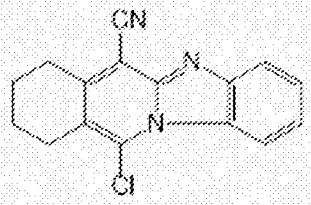
FIG. 1: illustrates exemplary compounds and biological activity.
Figure 1:
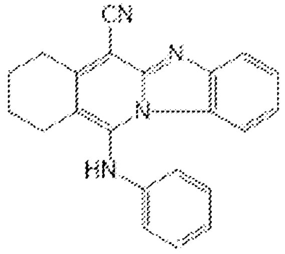
Figure 1:
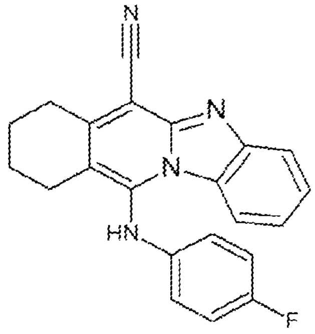
Figure 1:
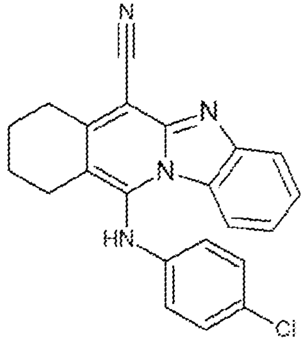
Figure 1:
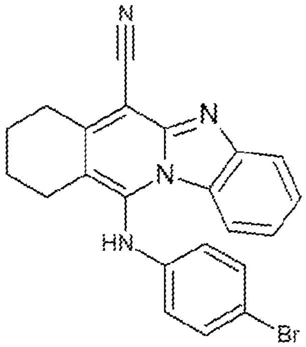
Figure 1:
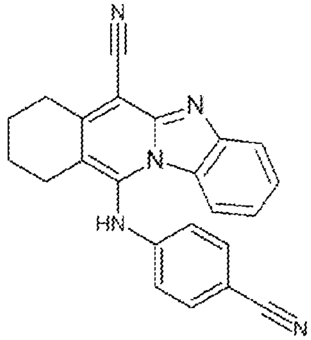
Figure 1:
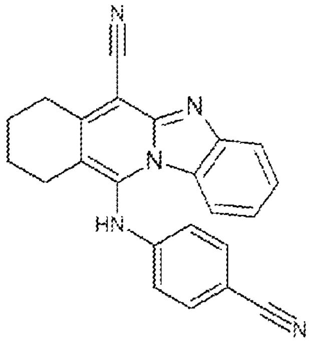
Figure 1:
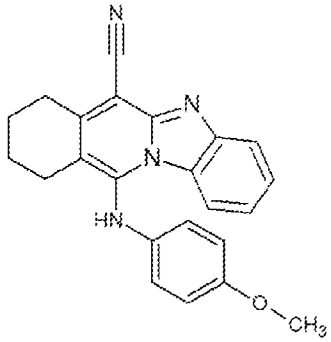
Figure 1:
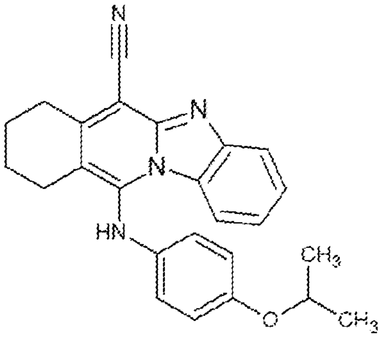
Figure 1:
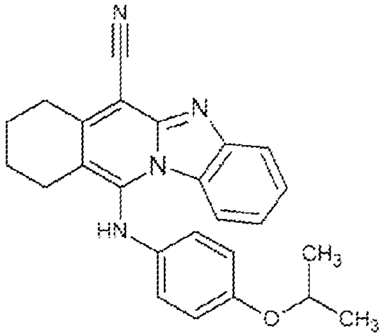
Figure 1:
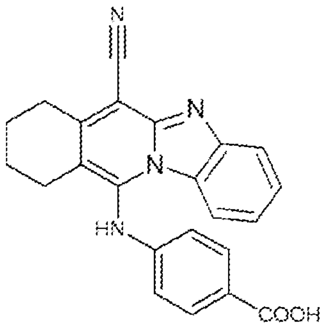
Figure 1:
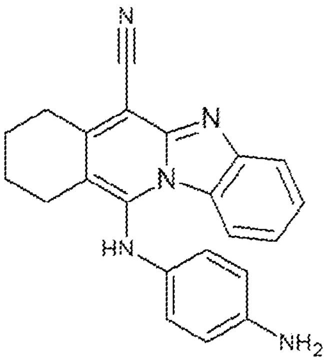
Figure 1:
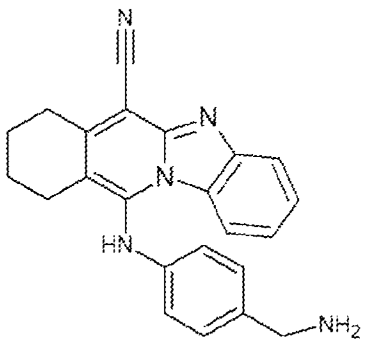
Figure 1:
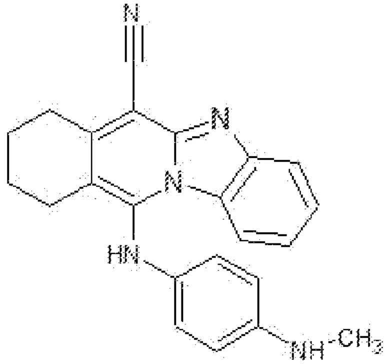
Figure 1:
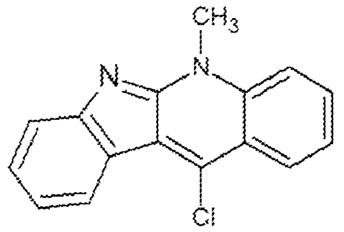
Figure 1:
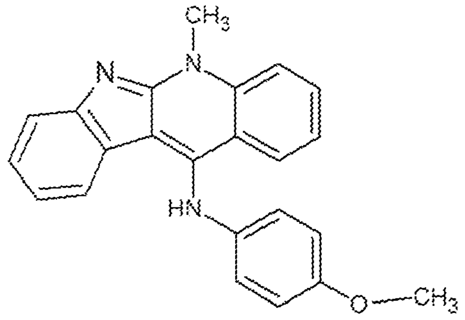
Figure 1:
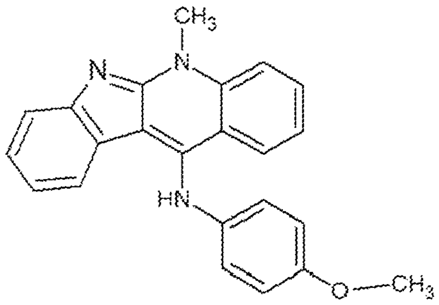

Disclosed herein are inhibitors of ubiquitin specific peptidase 22(USP22) and uses for treating diseases and disorders thereof. Computer-based and biological approaches were used to identify small molecule specific inhibitors of USP22. As demonstrated in the Examples, treatment of regulatory T cells (Tregs), both mouse and human, with inhibitors of USP22 significantly reduced the protein expression of FoxP3, a substrate of USP22. In contrast, treatment did not further inhibit FoxP3 expression in USP22-null Tregs, indicating that the inhibitors of USP22 are highly specific inhibitors of USP22. In addition, treatment inhibited USP22 activity in lung cancer cells and consequently suppressed lung cancer cell growth. More importantly, treatment of lung cancer-bearing mice largely diminished the tumor mass. These results indicate that inhibitors of USP22 can be used as a potent drug in antitumor therapy. In addition, the fact that suppression of USP22 diminishes Treg suppressive functions, also allows for these inhibitors to be used to treat diseases associated to immune deficiency as well as to boost the immune response to combat infectious diseases such as SARS-CoV2 infection.

The present invention is described herein using several definitions, as set forth below and throughout the application.

Definitions

The disclosed subject matter may be further described using definitions and terminology as follows. The definitions and terminology used herein are for the purpose of describing particular embodiments only and are not intended to be limiting.

As used in this specification and the claims, the singular forms “a,” “an,” and “the” include plural forms unless the context clearly dictates otherwise. For example, the term “a substituent” should be interpreted to mean “one or more substituents,” unless the context clearly dictates otherwise.

As used herein, “about”, “approximately,” “substantially,” and “significantly” will be understood by persons of ordinary skill in the art and will vary to some extent on the context in which they are used. If there are uses of the term which are not clear to persons of ordinary skill in the art given the context in which it is used, “about” and “approximately” will mean up to plus or minus 10% of the particular term and “substantially” and “significantly” will mean more than plus or minus 10% of the particular term.

As used herein, the terms “include” and “including” have the same meaning as the terms “comprise” and “comprising.” The terms “comprise” and “comprising” should be interpreted as being “open” transitional terms that permit the inclusion of additional components further to those components recited in the claims. The terms “consist” and “consisting of” should be interpreted as being “closed” transitional terms that do not permit the inclusion of additional components other than the components recited in the claims. The term “consisting essentially of” should be interpreted to be partially closed and allowing the inclusion only of additional components that do not fundamentally alter the nature of the claimed subject matter.

The phrase “such as” should be interpreted as “for example, including.” Moreover, the use of any and all exemplary language, including but not limited to “such as”, is intended merely to better illuminate the invention and does not pose a limitation on the scope of the invention unless otherwise claimed.

Furthermore, in those instances where a convention analogous to “at least one of A, B and C, etc.” is used, in general such a construction is intended in the sense of one having ordinary skill in the art would understand the convention (e.g., “a system having at least one of A, B and C” would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase “A or B” will be understood to include the possibilities of “A” or ‘B or “A and B.”

All language such as “up to,” “at least,” “greater than,” “less than,” and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb “may” refers to the preferred use or selection of one or more options or choices among the several described embodiments or features contained within the same. Where no options or choices are disclosed regarding a particular embodiment or feature contained in the same, the modal verb “may” refers to an affirmative act regarding how to make or use and aspect of a described embodiment or feature contained in the same, or a definitive decision to use a specific skill regarding a described embodiment or feature contained in the same. In this latter context, the modal verb “may” has the same meaning and connotation as the auxiliary verb “can.”

A “subject in need thereof” as utilized herein may refer to a subject in need of treatment for a disease or disorder associated with ubiquitin specific peptidase 22 (USP22) activity and/or expression. A subject in need thereof may include a subject having a cancer that is characterized by the activity and/or expression of USP22. The disclosed compounds, pharmaceutical compositions, and methods may be utilized to treat diseases and disorders associated with USP22 activity and/or expression.

In some embodiments, a subject in need thereof may include a subject having a cancer that is treated by administering a therapeutic agent that inhibits the biological activity of USP22, and/or that inhibits dissemination of cancer cells.

The disclosed compounds, pharmaceutical compositions, and methods may be utilized to treat diseases and disorders associated with USP22 activity and/or expression which may include cell proliferative diseases and diseases and disorders such as cancers. Suitable cancers for treatment by the disclosed compounds, pharmaceutical compositions, and methods may include, but are not limited to lung cancer, gastric carcinoma, pancreatic cancer, melanoma, lymphoma, colon cancer, breast cancer, ovarian cancer, bladder cancer, prostate cancer, glioma, mesothelioma, neuroblastoma, mantle cell lymphoma, and acute myeloid leukemia.

In some embodiments, a subject in need thereof may include a subject in need of treatment of infection. In some embodiments, the infection is a viral infection, such as an infection by a corona virus. In some embodiments, the subject in need thereof is in need of a treatment for infection by sudden acute respiratory syndrome coronavirus 2 (SARS-CoV2) and COVID. In some embodiments, a subject in need thereof may refer to a subject in need of augmenting the immune response to an infection. In some embodiments, a subject in need thereof may refer to a subject in need of augmenting the immune response to sudden acute respiratory syndrome coronavirus 2 (SARS-CoV2) infection.

The disclosed compounds, pharmaceutical compositions, and methods may be utilized to treat diseases and disorders associated with USP22 activity and/or expression which may include infections and diseases and disorders such as respiratory infections, including sudden acute respiratory syndrome coronavirus 2 (SARS-CoV2) infection.

The term “subject” may be used interchangeably with the terms “individual” and “patient” and includes human and non-human mammalian subjects.

The disclosed compounds may be utilized to modulate the biological activity of USP22, including modulating the peptidase activity of USP22. The term “modulate” should be interpreted broadly to include “inhibiting” USP22 biological activity including peptidase activity.

Ubiquitin specific peptidase (USP22) refers to the protein also referred to by the name ubiquitin carboxyl-terminal hydrolase 22. USP22 has been shown to have enzyme activities that include catalyzing the thiol-dependent hydrolysis of ester, thioester, amide, peptide and isopeptide bonds formed by the C-terminal glycine of ubiquitin. USP22 has ENZYME entry: EC 3.4.19.12. The compounds disclosed herein may inhibit one or more of the activities of USP22 accordingly.

Human USP22 is known to have two isoforms and the disclosed compounds may inhibit one or more activities of isoform 1 and/or isoform 2.

Human USP22 Isoform 1 has the following amino acid sequence:

```
                                   (SEQ ID NO.: 1)
        10         20         30         40
MVSRPEPEGE AMDAELAVAP PGCSHLGSFK VDNWKQNLRA

        50         60         70         80
IYQCFVWSGT AEARKRKAKS CICHVCGVHL NRLHSCLYCV

        90        100        110        120
FFGCFTKKHI HEHAKAKRHN LAIDLMYGGI YCFLCQDYIY

       130        140        150        160
DKDMEIIAKE EQRKAWKMQG VGEKFSTWEP TKRELELLKH

       170        180        190        200
NPKRRKITSN CTIGLRGLIN LGNTCFMNCI VQALTHTPLL

       210        220        230        240
RDFFLSDRHR CEMQSPSSCL VCEMSSLFQE FYSGHRSPHI

       250        260        270        280
PYKLLHLVWT HARHLAGYEQ QDAHEFLIAA LDVLHRHCKG

       290        300        310        320
DDNGKKANNP NHCNCIIDQI FTGGLQSDVT CQVCHGVSTT

       330        340        350        360
IDPFWDISLD LPGSSTPFWP LSPGSEGNVV NGESHVSGTT

       370        380        390        400
TLTDCLRRFT RPEHLGSSAK IKCSGCHSYQ ESTKQLTMKK

       410        420        430        440
LPIVACFHLK RFEHSAKLRR KITTYVSFPL ELDMTPFMAS

       450        460        470        480
SKESRMNGQY QQPTDSLNND NKYSLFAVVN HQGTLESGHY

       490        500        510        520
TSFIRQHKDQ WFKCDDAIIT KASIKDVLDS EGYLLFYHKQ FLEYE
```

Isoform 2 has the following sequence:

```
                                   (SEQ ID NO.: 2)
        10         20         30         40
MAPGWPSLSA GSRQEAPQLA AGGSAYQAVG RQFQPRATAL

        50         60         70         80
QGPSQAKSCI CHVCGVHLNR LHSCLYCVFF GCFTKKHIHE

        90        100        110        120
HAKAKRHNLA IDLMYGGIYC FLCQDYIYDK DMEIIAKEEQ

       130        140        150        160
RKAWKMQGVG EKFSTWEPTK RELELLKHNP KRRKITSNCT

       170        180        190        200
IGLRGLINLG NTCFMNCIVQ ALTHTPLLRD FFLSDRHRCE

       210        220        230        240
MQSPSSCLVC EMSSLFQEFY SGHRSPHIPY KLLHLVWTHA

       250        260        270        280
RHLAGYEQQD AHEFLIAALD VLHRHCKGDD NGKKANNPNH

       290        300        310        320
CNCIIDQIFT GGLQSDVTCQ VCHGVSTTID PFWDISLDLP

       330        340        350        360
GSSTPFWPLS PGSEGNVVNG ESHVSGTTTL TDCLRRFTRP

       370        380        390        400
EHLGSSAKIK CSGCHSYQES TKQLTMKKLP IVACFHLKRF

       410        420        430        440
EHSAKLRRKI TTYVSFPLEL DMTPFMASSK ESRMNGQYQQ
```

-continued

```
       450        460        470        480
PTDSLNNDNK YSLFAVVNHQ GTLESGHYTS FIRQHKDQWF

       490        500        510
KCDDAIITKA SIKDVLDSEG YLLFYHKQFL EYE
```

New Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched $C_1$-$C_6$ alkyl group). Exemplary alkylene groups include, but are not limited to $—CH_2—$, $—CH_2CH_2—$, $—CH_2CH_2CH_2—$, $—CH(CH_3)CH_2—$, $—CH_2CH(CH_3)CH_2—$, $—CH(CH_2CH_3)CH_2—$, and the like.

The term "haloalkyl" refers to an alkyl group that is substituted with at least one halogen. For example, $—CH_2F$, $—CHF_2$, $—CF_3$, $—CH_2CF_3$, $—CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido (or amidocarboxyl), amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido (or amidocarboxyl), carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —$R^1C(O)N(R^2)$—, —$R^1C(O)N(R^2)R^3$—, —$C(O)NR^2R^3$, or —$C(O)NH_2$, wherein $R^1$, $R^2$ and $R^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds and molecules may be designated by the symbols "R" or "S," or "+" or "−" depending on the configuration of substituents around the stereogenic carbon atom and or the optical rotation observed. The present invention encompasses various stereo isomers of these compounds and molecules and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds and molecules, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

The formulae of the compounds and molecules disclosed herein should be interpreted as encompassing all possible stereoisomers, enantiomers, or epimers of the compounds and molecules unless the formulae indicates a specific stereoisomer, enantiomer, or epimer. The formulae of the compounds and molecules disclosed herein should be interpreted as encompassing salts, esters, amides, or solvates thereof of the compounds and molecules.

Pharmaceutical Compositions

The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

The compounds for use according to the methods of disclosed herein may be administered as a single compound or a combination of compounds. For example, a compound that inhibits the biological activity of ubiquitin specific peptidase 22 (USP22) may be administered as a single compound or in combination with another compound inhibits the biological activity of USP22 or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds, which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counter-ion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated with the biological activity of ubiquitin specific peptidase 22 (USP22). As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with biological activity of ubiquitin specific peptidase 22 (USP22).

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition, and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

Inhibitors of Ubiquitin specific Peptidase 22 (USP22) Uses Thereof

Disclosed are compounds, pharmaceutical compositions comprising the compounds, and methods of using the compounds and pharmaceutical compositions for treating a subject having or at risk for developing a disease or disorder associated with ubiquitin specific peptidase 22 (USP22) biological activity. The disclosed compounds may inhibit the biological activity of USP22. As such, the disclosed compounds and pharmaceutical compositions may be utilized in methods for treating a subject having or at risk for developing a disease or disorder that is associated with USP22 activity which may be cell proliferative diseases and disorders, such as cancer, or an infection associated disease or disorder, such as sudden acute respiratory syndrome, such as SARS-CoV2.

In some embodiments, the disclosed methods include treating a subject in need of treatment for a disease or disorder associated with ubiquitin specific peptidase 22 (USP22) activity. In the disclosed methods, the subject may be administered an effective amount of a therapeutic agent that inhibits the biological activity of USP22.

The disclosed methods may be performed in order to treat a cell proliferative disease or disorder, which may include cancer. Suitable cancers that may be treated by the disclosed methods may include, but are not limited to, lung cancer, gastric carcinoma, pancreatic cancer, melanoma, lymphoma, colon cancer, breast cancer, ovarian cancer, bladder cancer, prostate cancer, glioma, mesothelioma, neuroblastoma, mantle cell lymphoma, and acute myeloid leukemia.

In some embodiments, the disclosed methods may be performed in order to treat lung cancer, for example, non-small cell lung cancer (NSCLC).

In some embodiments, the disclosed methods may be performed in order to treat skin cancer, for example, melanoma.

In the disclosed methods, a subject in need thereof typically is administered a therapeutic agent that inhibits the biological activity of ubiquitin specific peptidase 22 (USP22). In some embodiments, the therapeutic agent inhibits its ubiquitin specific peptidase activity (E.C.: 3.4.19.12) of USP22.

Suitable therapeutic agents for use in the disclosed methods may include, but are not limited to, a compound having a formula of (Ia)

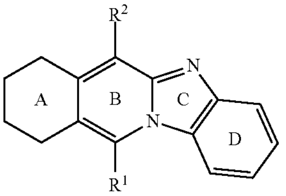

, (Ib)

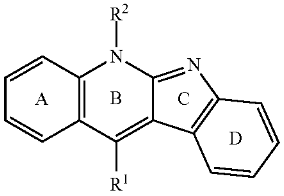

, or (Ic)

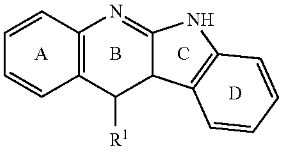

, or a pharmaceutically acceptable salt thereof, wherein $R^2$ is selected from cyano or alkyl and wherein $R^1$ is selected from —NH-phenyl, the phenyl is optionally substituted with halo (e.g., F, Cl, Br), —CN, alkyl, alkoxy (e.g., —OMe or —$OCH(CH_3)_2$), —$NO_2$, amino (e.g., —$NH_2$ or —NHMe), and —COOH and wherein the alkyl is optionally substituted with a halo (e.g., —$CF_3$) or amino (e.g., —$CH_3NH_2$), or halo.

In some embodiments, $R^1$ is —NH-phenyl, the phenyl substituted with halo, —CN, alkyl, alkoxy, —$NO_2$, amino, and —COOH and wherein the alkyl is optionally substituted with a halo or amino, or halo or $R^2$ is selected from alkyl and $R^1$ is —NH-phenyl, the phenyl optionally substituted with halo, —CN, alkyl, alkoxy, —$NO_2$, amino, and —COOH and wherein the alkyl is optionally substituted with a halo or amino, or halo.

In some embodiments, $R^1$ is —NH-phenyl, the phenyl substituted with halo, —CN, alkyl, alkoxy, —$NO_2$, amino, and —COOH and wherein the alkyl is optionally substituted with a halo or amino, or halo.

In some embodiments, $R^2$ is selected from alkyl and $R^1$ is —NH-phenyl, the phenyl optionally substituted with halo, —CN, alkyl, alkoxy, —$NO_2$, amino, and —COOH and wherein the alkyl is optionally substituted with a halo or amino, or halo.

In some embodiments, the compound has the formula Ia. In some instances where the compound of formula Ia, $R^1$ and $R^2$ are not cyano and —NH-phenyl, respectively.

In some embodiments, the compound has the formula Ib.

In some embodiments, the compound has the formula Ic.

In some embodiments, the compound has the formula II (II)

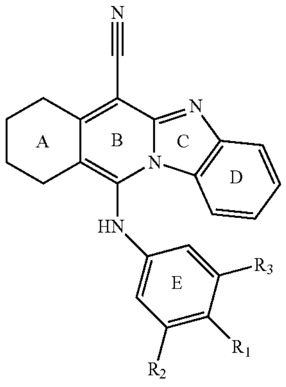

or a pharmaceutically acceptable salt thereof, wherein $R_1$ and $R_2$ are independently selected from hydrogen, halo (e.g., F, Cl, Br), —CN, alkyl, alkoxy (e.g., —OMe or —$OCH(CH_3)_2$), —$NO_2$, amino (e.g., —$NH_2$ or —NHMe), and —COOH, wherein the alkyl is optionally substituted with a halo (e.g., —$CF_3$) or amino (e.g., —$CH_3NH_2$).

In some instances where the compound of formula II, $R_1$, $R_2$, and $R_3$ are not each hydrogen.

In some embodiments, the compound is selected from

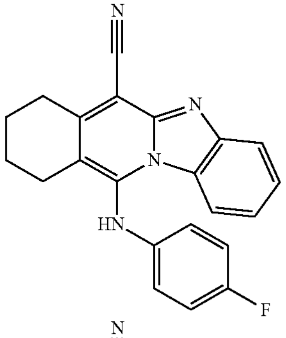

,

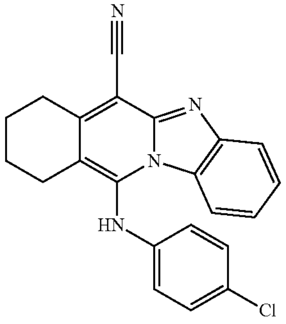

,

-continued
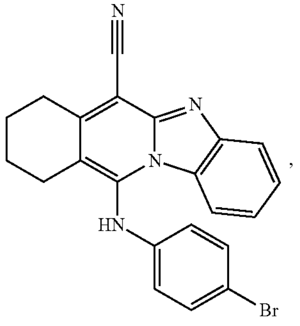
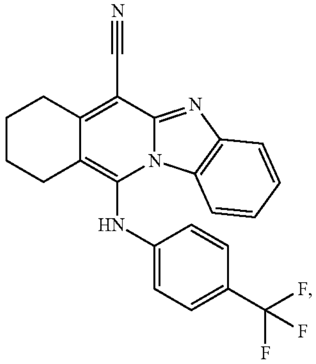
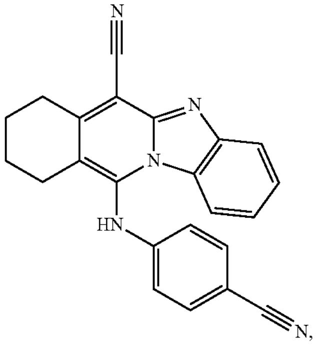
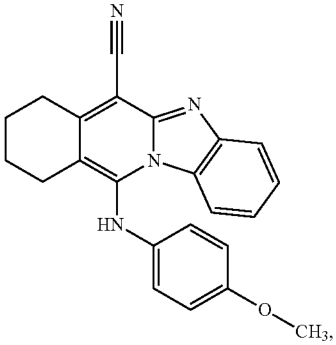
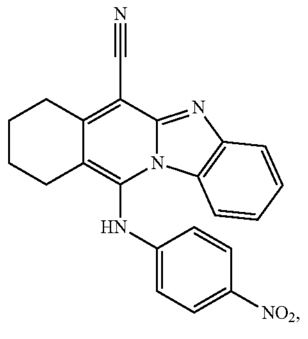
-continued
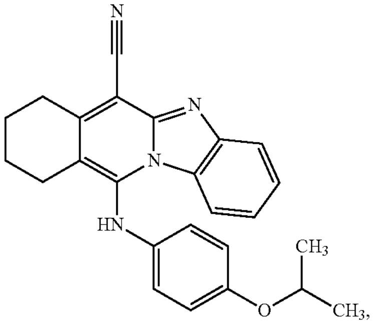
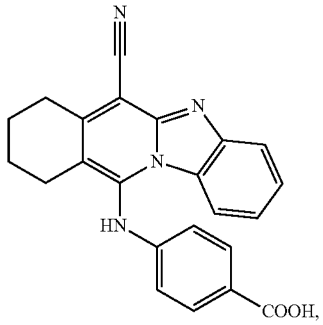
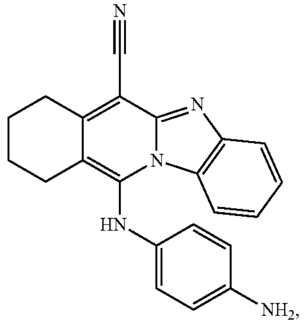
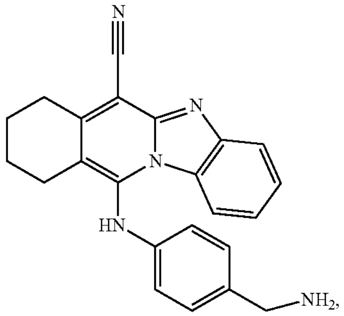
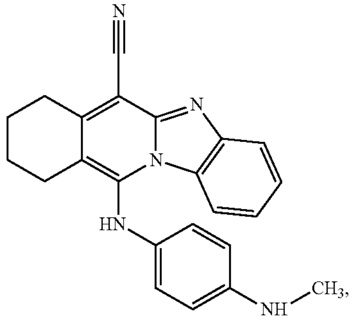

-continued

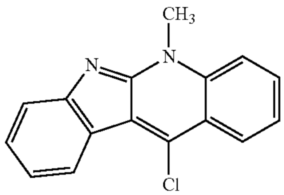

,

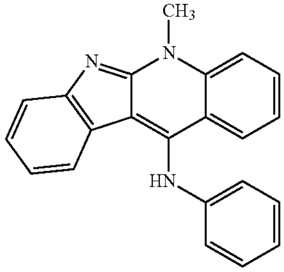

,

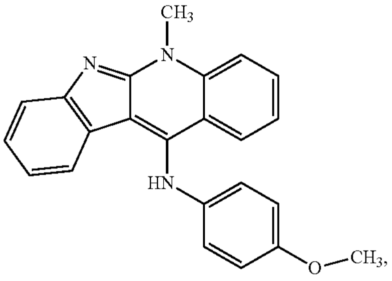

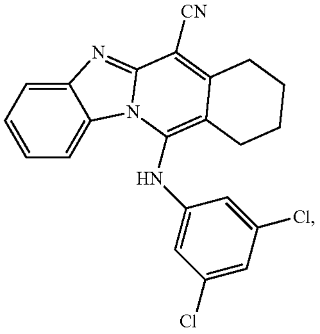

and

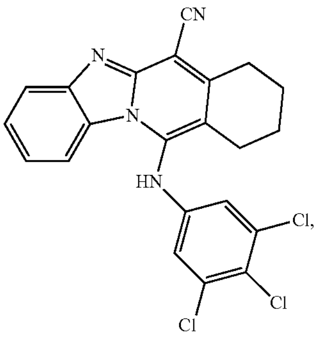

In some embodiments, the compounds of Formula Ia, Ib, Ic, or II specifically exclude one or more of the foregoing compounds.

In some embodiments, the compound is

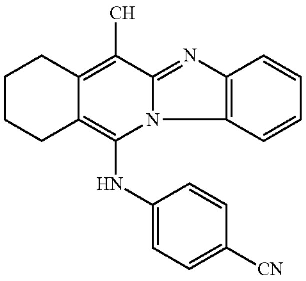

In some embodiments, the compound is

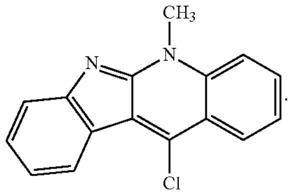 [SMILES: Cn1c2nc3ccccc3c-2c(Cl)c2ccccc21]

In some embodiments, the compound is selected from

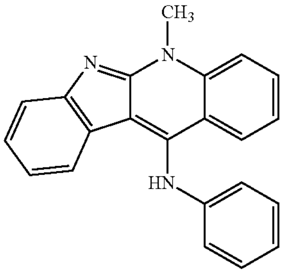

or

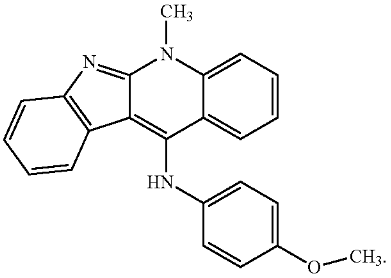

The disclosed methods also may be performed in order to suppress Treg cell activity in a subject in need thereof. For example, in the disclosed methods the subject may be administered an effective amount of a therapeutic agent that inhibits the activity of USP22, thereby suppressing Treg cell activity in the subject.

In some embodiments, the disclosed methods may also be performed in order to augment the immune response of the subject to an infectious disease in a subject in need thereof.

In some embodiments, the disclosed methods are used to augment the immune response to sudden acute respiratory syndrome coronavirus 2 (SARS-CoV2) infection in a subject in need thereof.

In some embodiments, the disclosed methods are used to augment the immune response of the subject to an infectious disease, in a subject in need thereof. In some embodiments, the therapeutic agent inhibits ubiquitin specific peptidase activity (E.C.: 3.4.19.12) of USP22.

In some embodiments, the disclosed methods of augmenting a subject's immune response to an infectious disease. For example, the therapeutic agent administered to a subject in a need thereof may be a compound having a formula selected from any of the compounds described herein.

Also disclosed are pharmaceutical compositions. In some embodiments, the disclosed pharmaceutical compositions comprise an effective amount of a therapeutic agent that inhibits the biological activity of ubiquitin specific peptidase 22 (USP22).

In some embodiments, the disclosed pharmaceutical compositions comprise an effective amount of a therapeutic agent having a formula chosen from any of the compounds described herein and a suitable pharmaceutical carrier.

In some embodiments of the disclosed pharmaceutical compositions, the pharmaceutical compositions may comprise an effective amount of a compound is selected from any of the compounds described herein and a suitable pharmaceutical carrier.

In some embodiments, the disclosed pharmaceutical composition may comprise an effective amount of 11-Anilino-7,8,9,10-tetrahydrobenzimidazo[1,2-b]isoquinoline-6-carbonitrile and a suitable pharmaceutical carrier.

In some embodiments, the disclosed pharmaceutical compositions may comprise an effective amount of the compound for inhibiting the biological activity of USP22 when administered to a subject in need thereof.

EXAMPLES

The following Examples are illustrative and should not be interpreted to limit the scope of the claimed subject matter.

Figure 5:
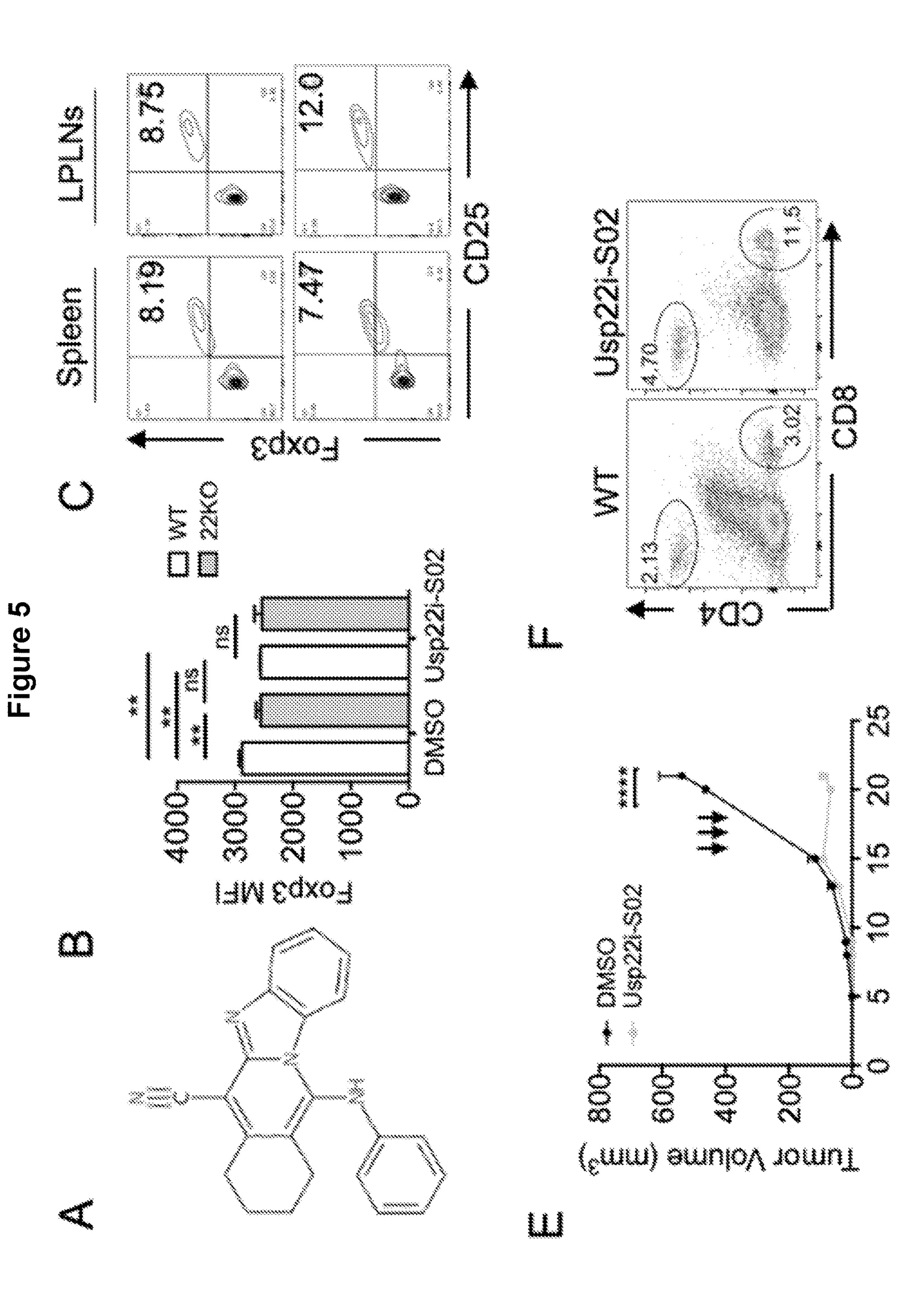
FIG. 5: Usp22 inhibitor administration enhances antitumor immunity. A, Structure of compound CS30 (Usp22i-S02). B, FOXP3 MFI in WT and 22KO of $T_{reg}$ cells after treatment with 20 μg/kg of Usp22i-S02 in vivo (n=3). C, Representative flow cytometry plot of FOXP3+CD25+MFI of CD4+ peripheral cells of mice treated with 20 μg/kg of Usp22i-S 02 relative to control (n=5). D, Graphical representation of Foxp3 MFI upon Usp22i-S02 administration (n=5). E, Tumor growth curve of LLC1 cells subcutaneously injected in the flank of WT mice with or without the addition of 20 mg/kg/time of the Usp22 inhibitor starting at day 15, in 100 μL of oil (n=4). F-G, Representative flow cytometry plot and graphical representation of % infiltration of CD4+ and CD8+ T cells within the tumor (n=4). H, Representative histogram plot and graphical representation of intratumoral Treg (itTreg) Foxp3 MFI (n=4). I, MFI of itTreg suppressive markers (n=3-4). J, Percent Foxp3+IFNg+itTreg cells in control and Usp22-S02 treated mice (n=3-4). B, D-E, G, H-I Two-way ANOVA with multiple comparisons between rows was performed to determine statistical significance. J, Unpaired two tailed T test was performed to determine significance. All data are presented as mean±stdev. NS, not significant. *P<0.05, P<0.01, *P<0.001, ****P<0.0001.
Figure 5:
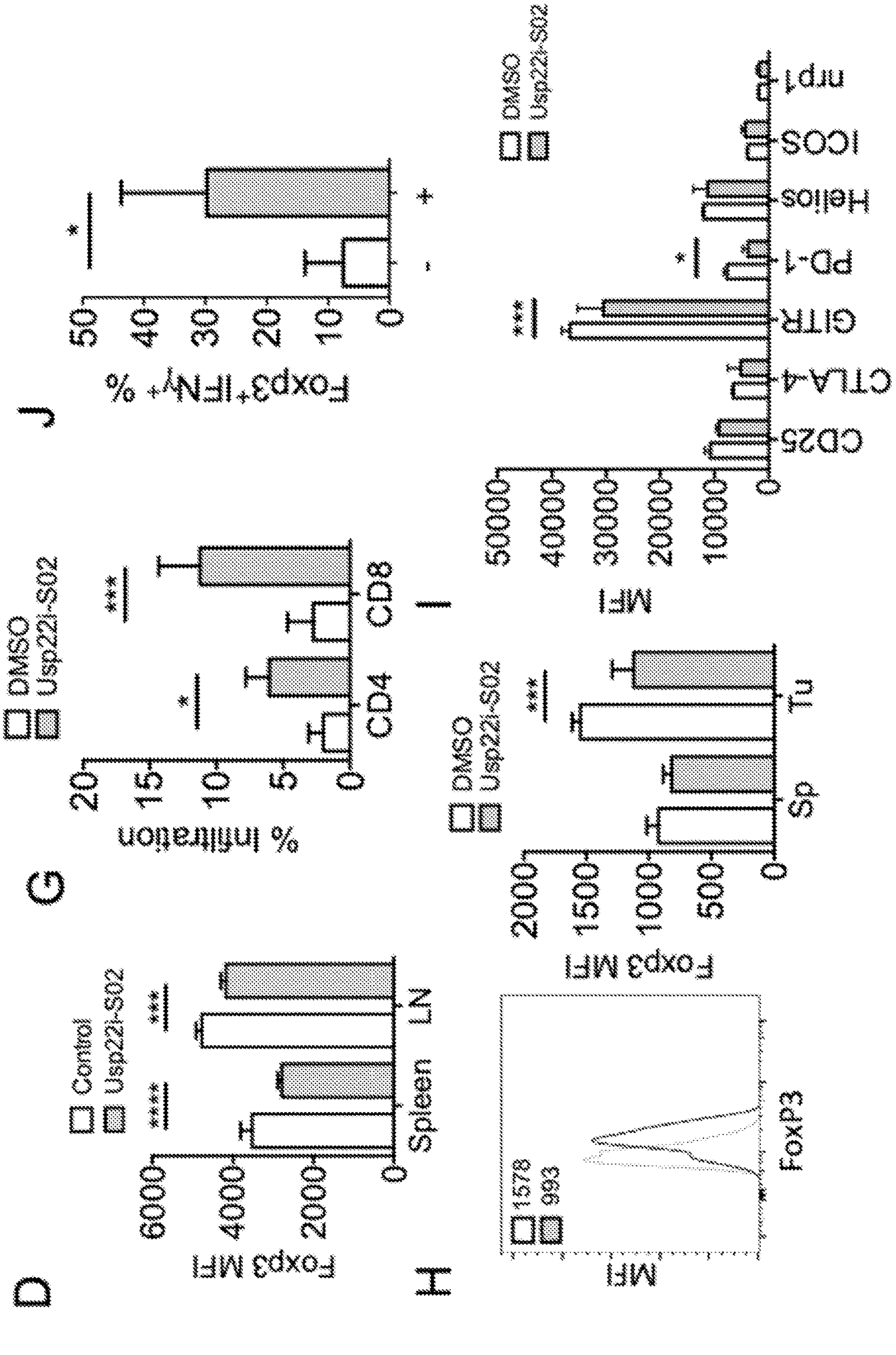
Figure 6:
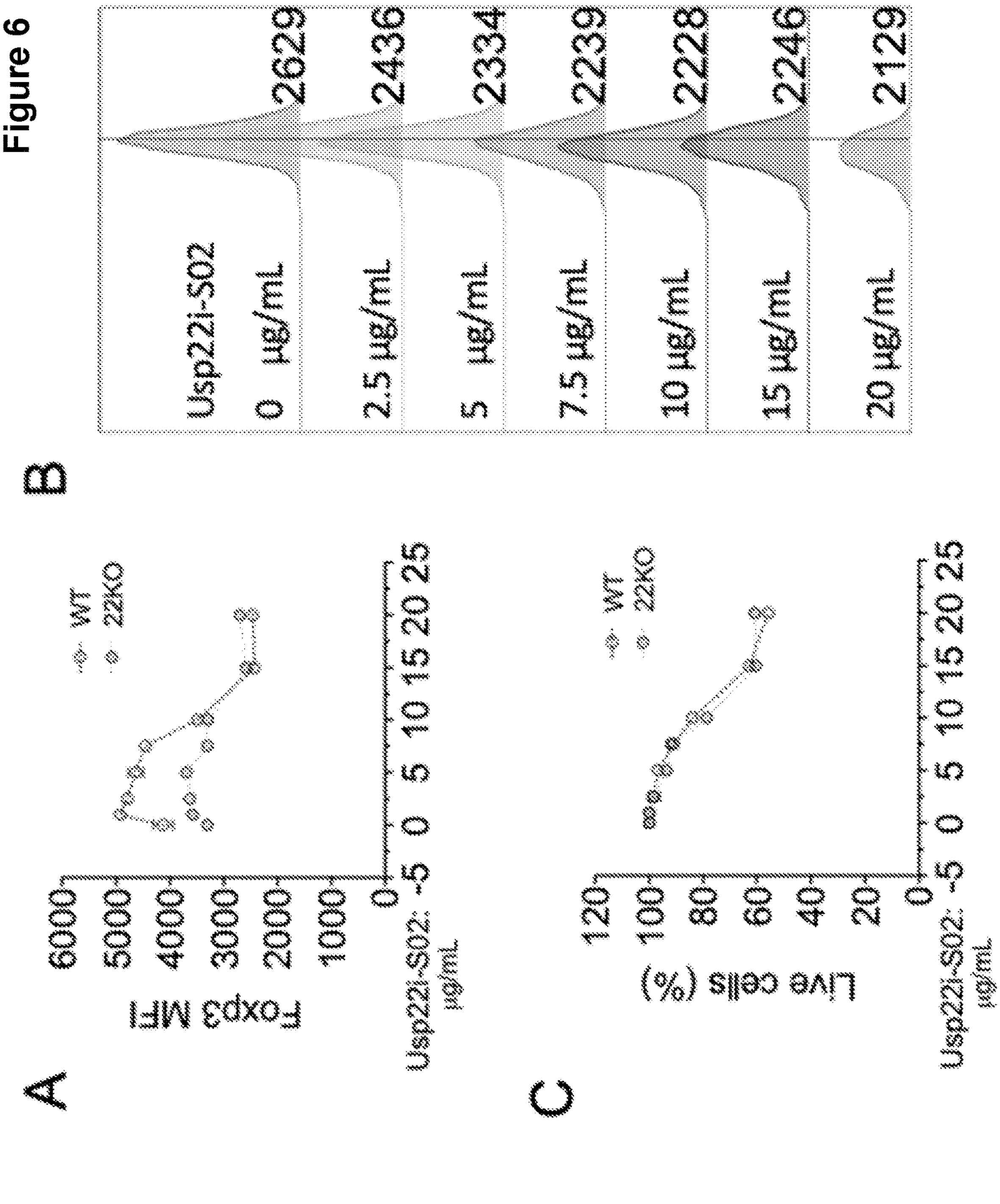
FIG. 6: Usp22i-S02 halts Usp22-mediated Foxp3 deubiqutination. A, Graphical representation of Foxp3 MFI change in WT versus 22KO iTreg cells treated with various doses of Usp22i-S02 (n=3). B, Representative histogram of Foxp3 MFI level in iTreg cells as Usp22 inhibitor concentration increases from 0-20 μg/mL. C, Cell survival of iTreg cells treated with various doses of Usp22i-S02 (n=3). D, FOXP3 and USP22 protein level in WT and 22KO mice treated with 10 μg/mL Usp22i-S02. E-F, Graphical and representative data of Foxp3 MFI of human Treg cells treated with various doses of Usp22i-S02 (n=3). G, Graphical representation of Foxp3 MFI in WT, Usp21-null, and Usp22-null Treg cells treated with Usp22i-S02 at 10 μg/mL (n=3). H, FOXP3 and USP22 protein degradation of cycloheximide (10 μg/mL) treated iTreg cells with or without the addition of 10 μg/mL of Usp22i-S02. I-J, Endogenous DUB assay IP in iTreg cells of USP22 with FOXP3 under increasing concentrations of Usp22i-S02. K, Foxp3 mRNA level in iTreg cells as Usp22 inhibitor concentration increases from 0-20 μg/mL (n=3). L, FOXP3 and USP22 level in WT iTreg cells with or without 20 μg/mL Usp22 inhibitor treated with 20 μM MG132. M, Graphical representation of the percentage of decrease of Foxp3 MFI in either WT or Usp22-null nTreg cells placed in low glucose conditions with or without the addition of 10 μg/mL of Usp22i-S02 (n=7-8). N, Graphical representation of the percentage of decrease of Foxp3 MFI in WT nTreg cells placed in hypoxic or low amino acid conditions with or without the addition of 10 μg/mL of Usp22i-S02 (n=3-5). G, Two-tailed unpaired t-test comparing within groups was performed to determine statistical significance. K, One-way ANOVA with Dunnet's multiple comparisons between rows relative to control was performed to determine statistical significance. M-N, Two-way ANOVA with Sidak's multiple comparisons between rows was performed to determine statistical significance. All data are presented as mean±stdev. NS, not significant. *P<0.05, P<0.01, *P<0.001, ****P<0.0001.
Figure 6:
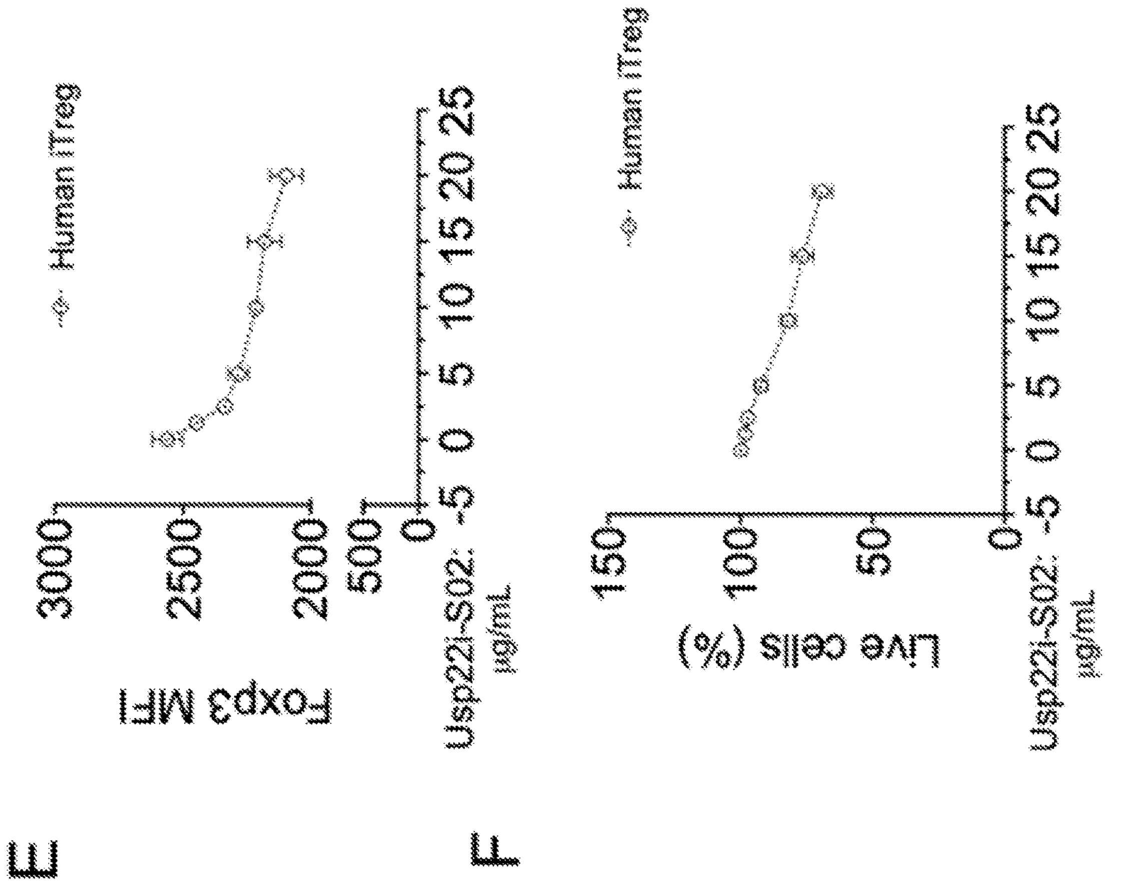
Figure 6:
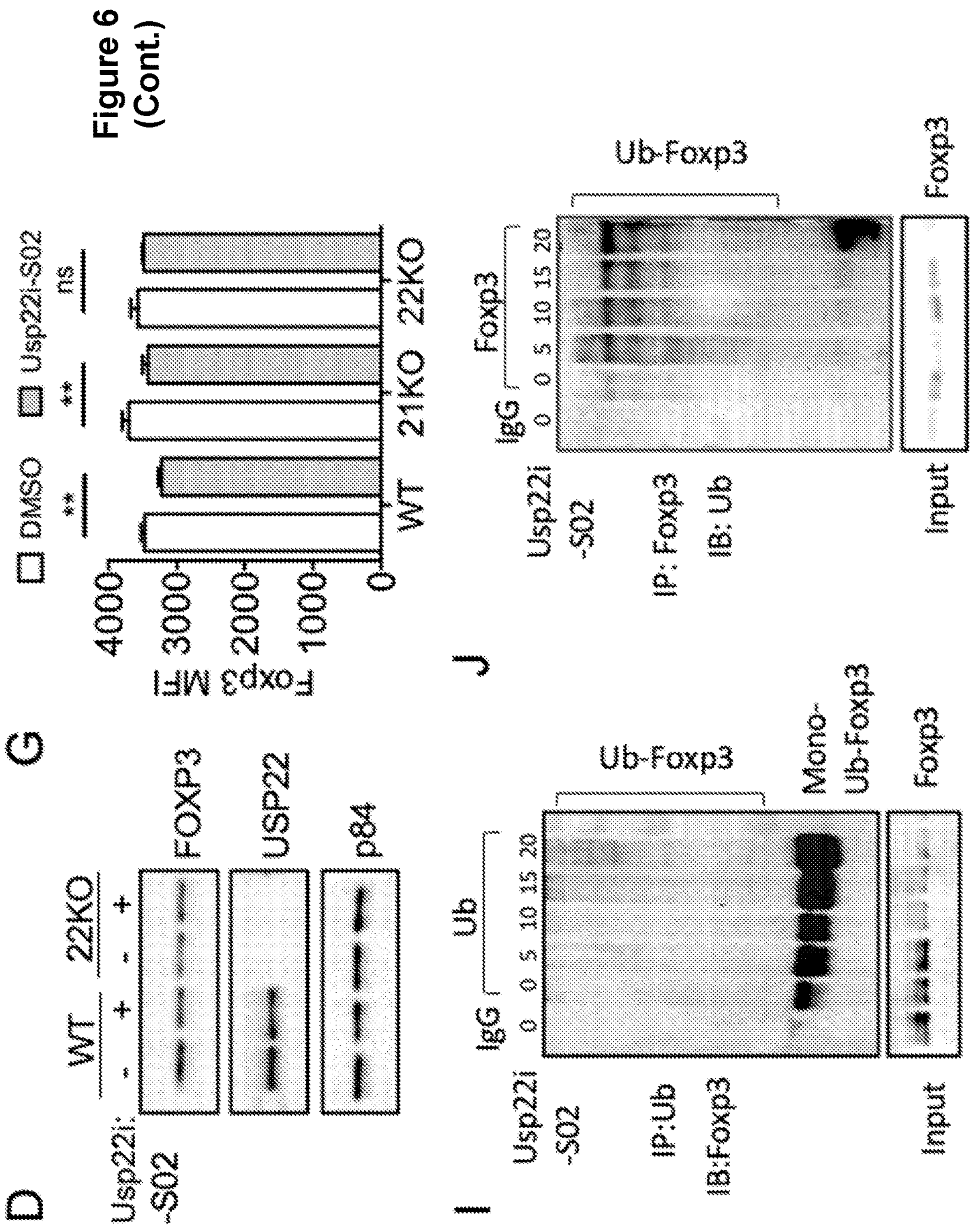
Figure 6:
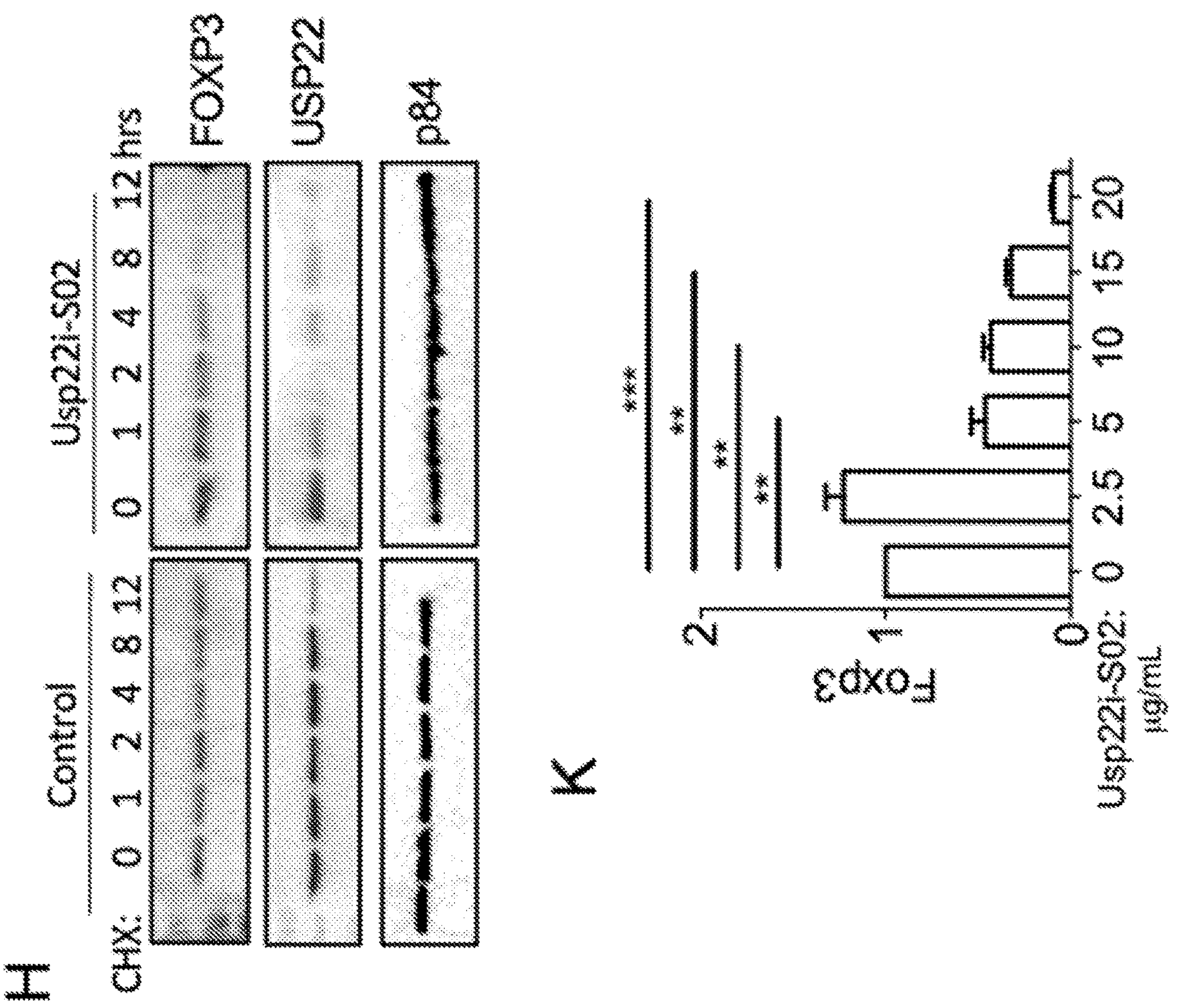
Figure 6:
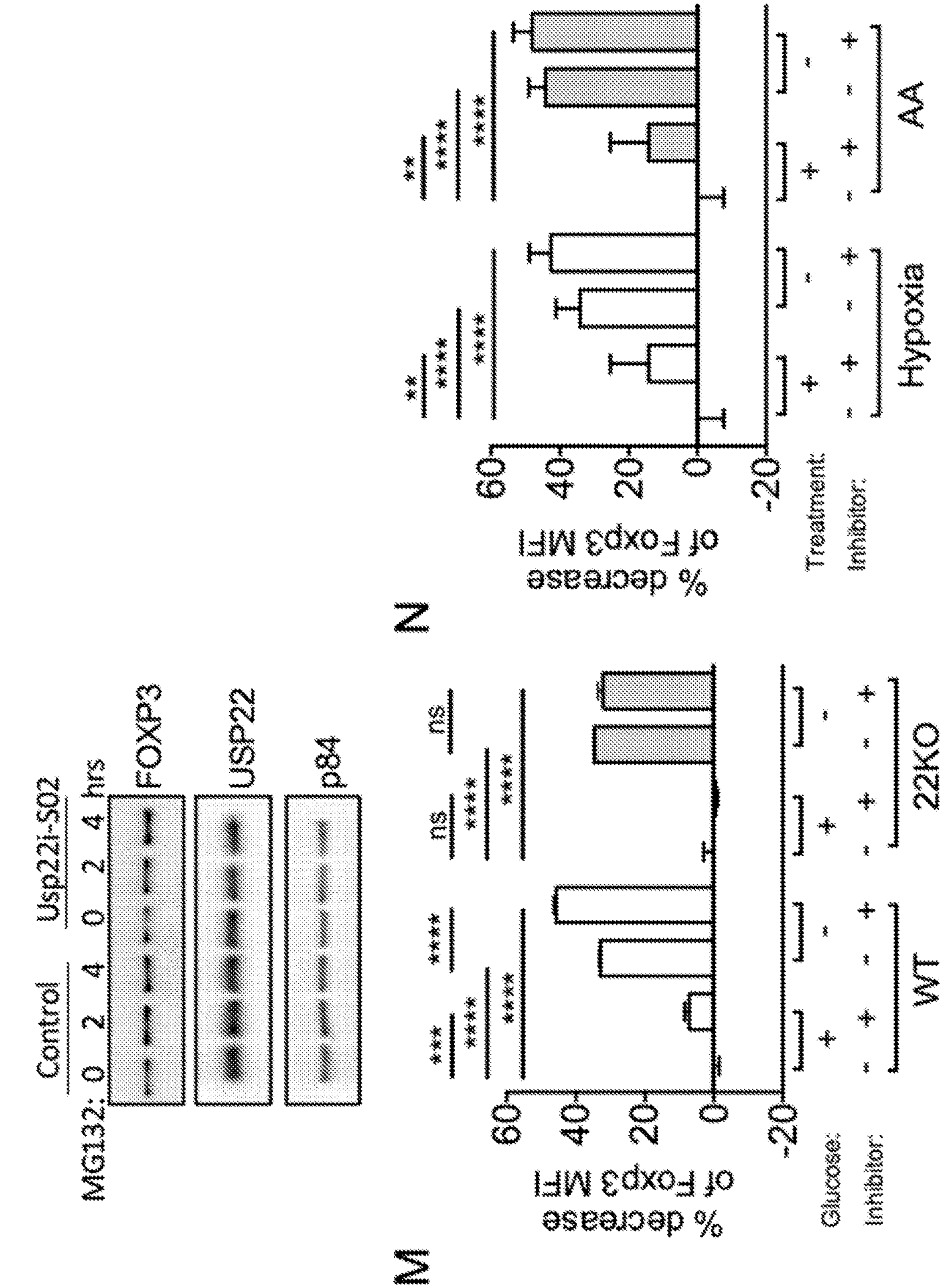

Example 1—Usp22i-S02 Holds Preclinical Efficacy in Enhancing Anti-Tumor Immunity After initial screening, we ran an in vitro dose response study on compound S02, dubbed Usp22i-S02, in both WT and Usp22-null i$T_{reg}$ cells (FIG. 6A-C). A concentration of 10 μg/mL showed decreases in Foxp3 MFI and protein level comparable to Usp22-null i$T_{reg}$ cells with little effect on viability, indicating a near complete suppression of Usp22 activity in stabilizing Foxp3 (FIG. 6A-D). Importantly, low doses of Usp22i-S02 administration to human $T_{reg}$ cells significantly decreased Foxp3 MFI with little effect to cell viability, showing the relevance of this inhibitor to human cells (FIGS. 6E and 6F). In contrast, Usp22i-S02 had minimal effect on FOXP3 levels in murine $T_{reg}$ cells already lacking Usp22 both in vivo (FIG. 5B) and in vitro, while having full effect on i$T_{reg}$ cells lacking Usp21 (FIGS. 6A and 6G). Functionally, Usp22i-S02 administration had similar effects to Usp22 deletion in i$T_{reg}$ cells, resulting in enhanced FOXP3 degradation in cycloheximide (CHX) treated cells, increased FOXP3 ubiquitination, and decreased Foxp3 transcription (FIG. 6H-K). Furthermore, Usp22i-S02-mediated FOXP3 degradation was halted by MG132 protease inhibition, indicating that Usp22i-S02 enhances proteasomal-specific degradation of FOXP3 (FIG. 6L). Importantly, Usp22i-S02 significantly diminished Foxp3 stability in $T_{reg}$ cells under glucose starvation, while having no effect on Foxp3 in $T_{reg}$ cells lacking Usp22 (FIG. 6M). This trend was also seen under hypoxic and amino acid starvation conditions, indicating that Usp22i-S02 reduces Foxp3 stability under TME factors (FIG. 6L). Therefore, these results indicate that Usp22i-S02 is a potent USP22-specific small molecule inhibitor that downregulates Foxp3 expression in $T_{reg}$ cells.

Figure 7:
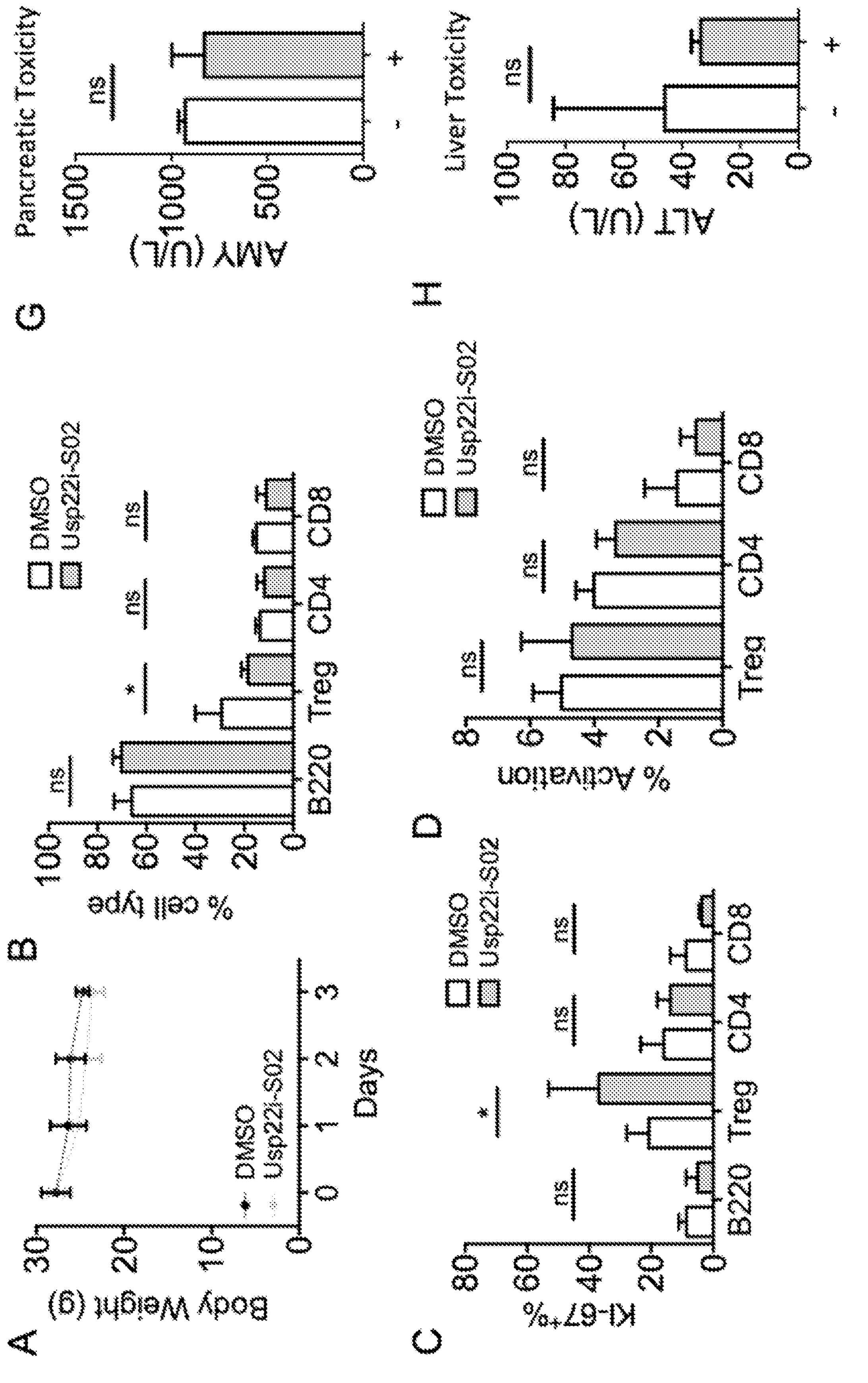
FIG. 7: Usp22i-S02 has little effect on naïve mice, yet enhances anti-tumor immunity in LLC1-challenged mice. A, Body weight of Usp22i-S02 treated mice verses DMSO treated controls over the course of treatment (n=4). A-F. Injections were twice a day for 3 consecutive days at 10 μg/kg (n=4). B, Percent of cell populations in naïve mice treated with Usp22i-S02 relative to DMSO control (n=3-4). C, Percent of KI-67+ cells in various compartments in naïve mice treated with Usp22i-S02 relative to DMSO control (n=3-4). D, Percent $CD44^{hi}CD62L^{lo}$ in T cell populations gated on CD45+ cells in naïve mice treated with Usp22i-S02 relative to DMSO control (n=3). E, Percent Annexin+PI+ T cells gates on CD45+ cells in naïve mice treated with Usp22i-S02 relative to DMSO control (n=4). F-H, Organ toxicity panel (VetScan VS2 Comprehensive Diagnostic Rotor lot 1061AA2) of naïve mice treated with Usp22i-S02 relative to DMSO control (n=2-3). I, Growth curve of subcutaneously injected LLC1 in WT mice treated with Usp22i-S02 at 10 μg/kg (n=5-10). I-Q, Injections were twice a day for 5 consecutive days at 10 μg/kg. J, Weights of resected tumors at day 16 from I (n=10). K-L, Representative flow plot and graphical representation of infiltrating T cells gated on CD45+ cells (n=5). M-P, Characterization of intratumoral CD8+ T cells frome mice treated with Usp22i-S02 (n=3-5). Q, Percent of intratumoral $T_{reg}$ cells from mice treated with Usp22i-S02 verses DMSO control, gated on CD4+Foxp3+ from mice (n=5). A-E, I and L, Two-way ANOVA with Sidaks's multiple comparisons between rows relative to control was performed to determine statistical significance. F-H, J, and M-Q, Two-tailed unpaired t-test was performed to determine statistical significance. All data are presented as mean±stdev. NS, not significant. *P<0.05, P<0.01, *P<0.001, ****P<0.0001.
Figure 7:
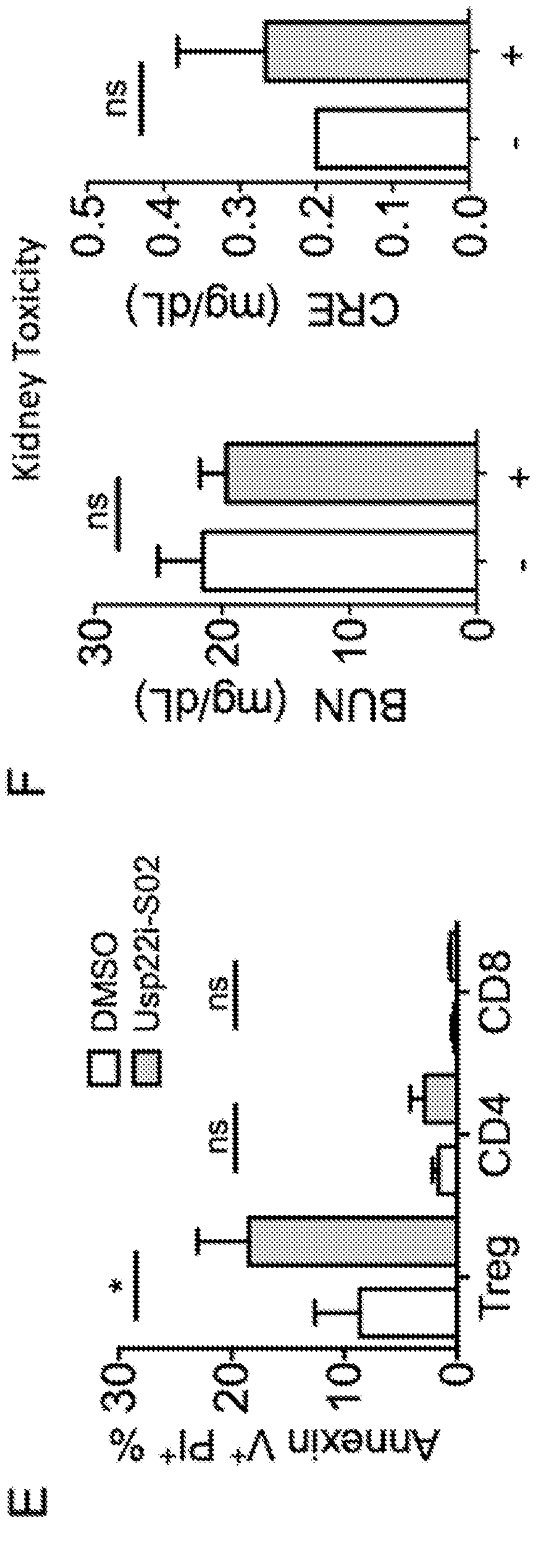
Figure 7:
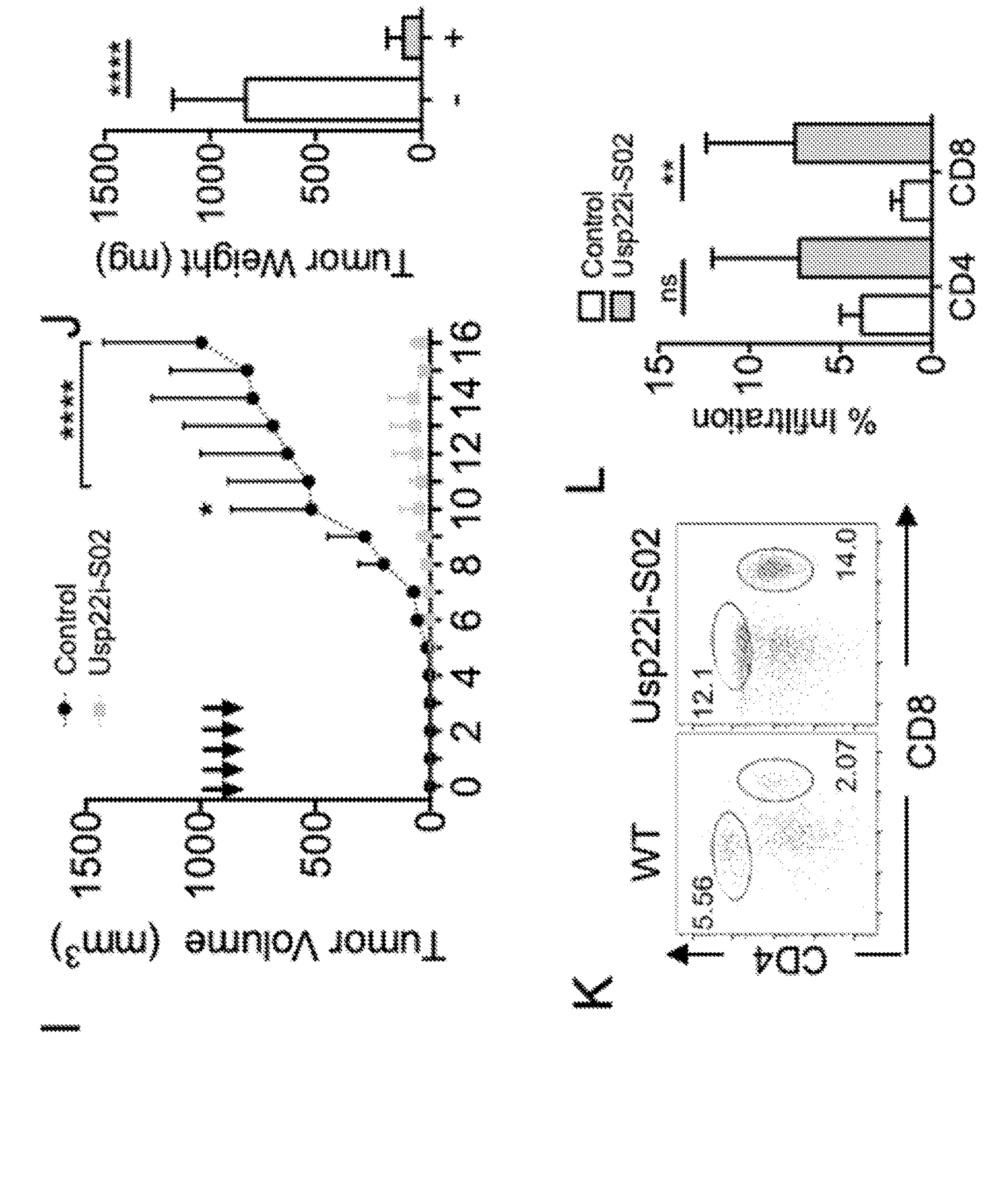
Figure 7:
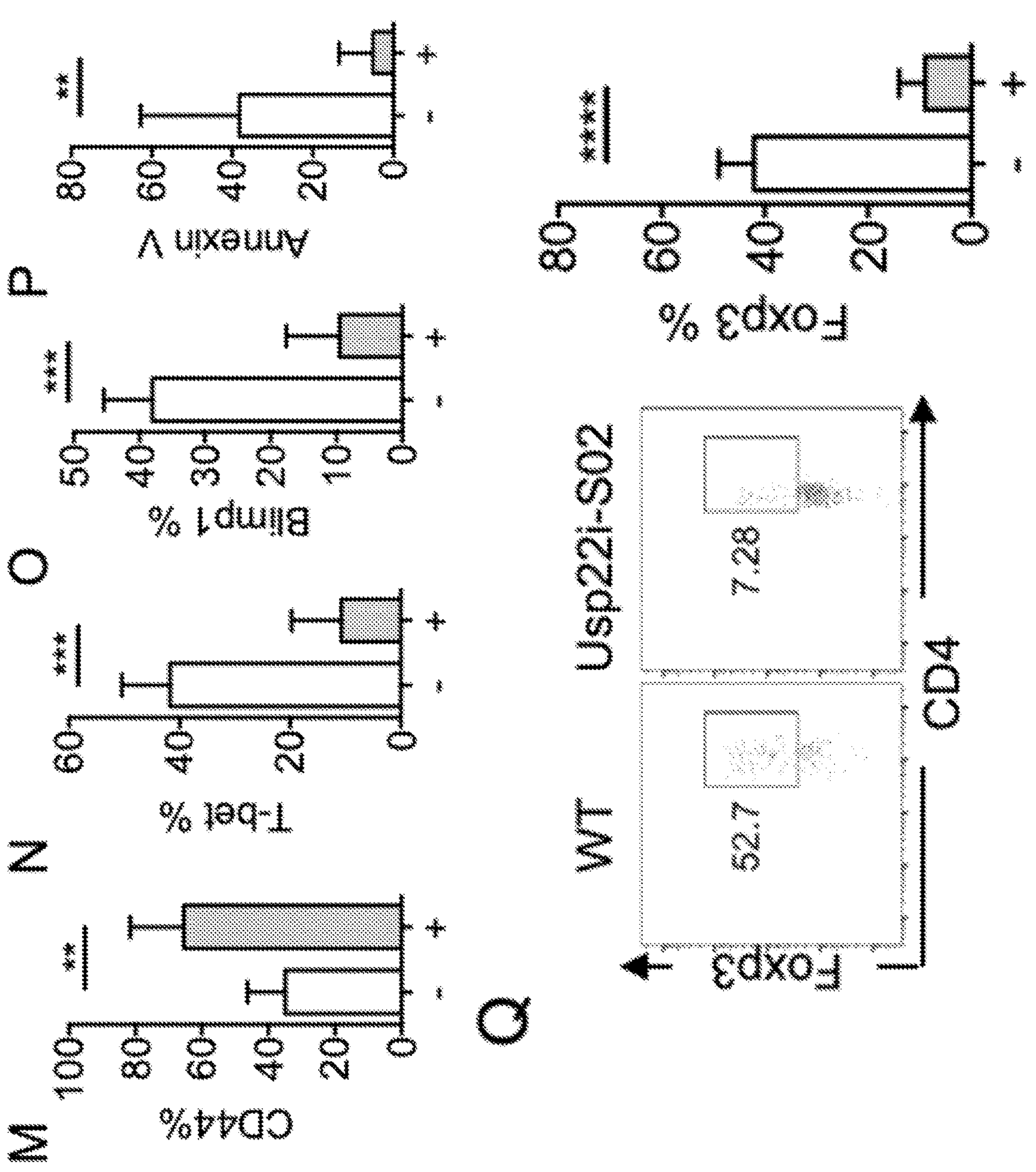

An important aspect of a potential immunotherapeutic is its antitumor functionality paired with low immune toxicity. To determine the toxicity of Usp22i-S02 in vivo, we first determined its effects in naïve mice. We found little alteration in the weights, B cell and $T_{eff}$ cell percentages and proliferation, and $T_{eff}$ cell activation of treated mice compared to DMSO-treated control mice (FIG. 7A-D). Unlike $T_{eff}$ cells, $T_{reg}$ cell death was significantly increased (FIG. 7E), resulting in a decrease in $T_{reg}$ percentage (FIG. 7B). Interestingly, $T_{reg}$ proliferation was also increased (FIG. 7C), potentially indicating a dysfunctional $T_{reg}$ population within the tumor. Importantly, administration of Usp22i-S02 to WT mice mimicked a genetic deletion of Usp22 in $T_{reg}$ cells, showing a significant drop in FOXP3 MFI in $T_{reg}$ cells from the spleen and lymph nodes without any alteration in $T_{reg}$ cell frequency, with no additional decrease to FOXP3 MFI in the Usp22-KO mice (FIG. 5B-D). Furthermore, a comprehensive tissue panel showed no organ toxicity differences form control DMSO treated mice (FIG. 7F-H). These data indicate that administration of Usp22i-S02 results in a $T_{reg}$-specific phenotype in naïve mice with little effects on other immune cell types and tissue toxicity.

To determine the functionality of Usp22i-S02 as a potential therapeutic, we tested the inhibitor on established tumors. Following initial LLC1 tumor establishment, WT mice administered Usp22i-S02 showed striking tumor rejection compared to untreated mice, as well as a significant increase in $T_{eff}$ cell tumor infiltration (FIG. 5E-G). Importantly, intratumoral, but not splenic, Foxp3$^+$ $T_{reg}$ percentage significantly decreased following administration of Usp22i-S02 (FIG. 6H). Furthermore, it$T_{reg}$ cells had lower levels of GITR and PD-1, and also expressed significantly higher levels of IFN-γ, a marker of $T_{reg}$ dysfunction and fragility (42), suggesting the importance of Usp22i-S02 on $T_{reg}$ cells specifically within the tumor (FIG. 5J). Further analysis of tumor infiltrating lymphocytes was done on mice treated immediately following tumor implantation (FIG. 7I). Along with decreased tumor burden and increased $T_{eff}$ cell infiltration, intratumoral CD8$^+$ T cells displayed a less exhausted phenotype, with an increase in CD44$^+$ cells and a decrease in T-bet$^{30}$ , Blimp1$^+$, and Annexin V$^+$ cells compared to non-treated mice (FIG. 7H-P). Importantly, intratumoral Foxp3$^+$ $T_{reg}$ percentage significantly decreased following administration of Usp22i-S02 (FIG. 7Q).

Figure 8:
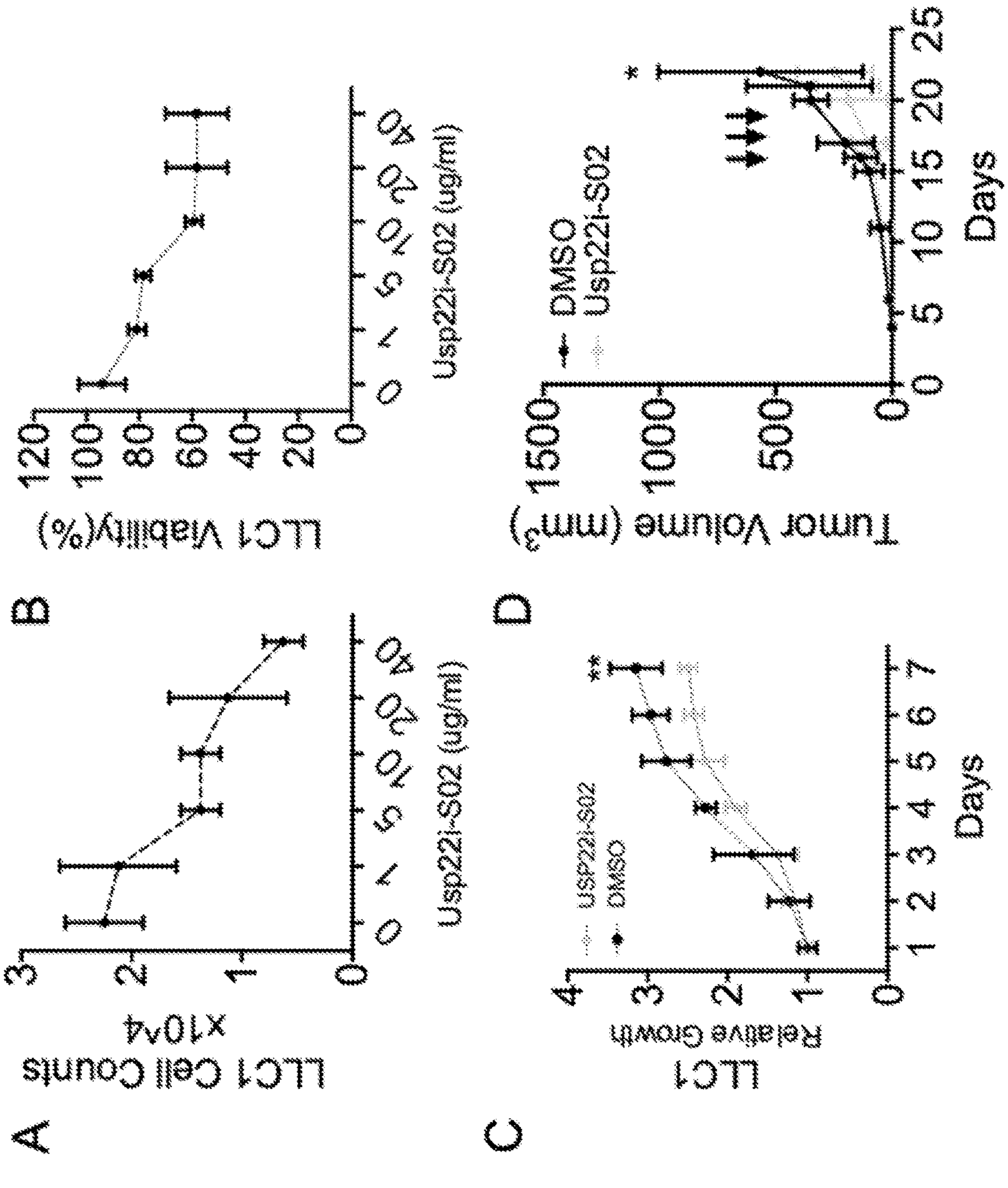
FIG. 8: Usp22i-S02 inhibits tumor growth in vitro and in vivo. A, In vitro counts of LLC1 after treatment with Usp22i-S02 under various concentrations for 24 hours (n=2). B, In vitro viability of LLC1 after treatment with Usp22i-S02 under various concentrations for 24 hours (n=2). C, In vitro relative growth of LLC1 cells treated with 10 ug/ml of Usp22i-S02 relative to DMSO treated control for 7 days via OD600 (n=4). D, Growth curve of 1 million subcutaneously injected LLC1 cells into RAG−/− mice treated for 3 days Usp22i-S02 relative to DMSO control injections at day 15 of tumor growth (n=4). C-D, Two-way ANOVA with Sidaks's multiple comparisons between rows relative to control was performed to determine statistical significance. All data are presented as mean±stdev. NS, not significant. *P<0.05, P<0.01, *P<0.001, ****P<0.0001.

As Usp22 is also an important oncogene, we were interested in the potential dual-therapeutic function of Usp22i-S02. Indeed, administration of Usp22i-S02 to LLC1 cells in vitro resulted in decreased tumor cell counts, viability, and growth (FIG. 8A-C). Furthermore, treatment of Rag$^{-/-}$ mice with established tumors resulted in a small but statistically significant decrease in tumor growth, in line with previous observations that tumor cell intrinsic Usp22 is required for tumor growth (FIG. 8D). Together, our data show the critical role of Usp22 in $T_{reg}$ cell stability and adaptation within the TME, and that specifically targeting Usp22 with a small molecule inhibitor enhances anti-tumor immunity through both tumor and immune intrinsic mechanisms.

11-anilino-7,8,9,10-tetrahydrobenzimidazo[1,2-b]isoquinoline-6-carbonitrile is a USP22-specific inhibitor. This inhibitor appears to be an antitumor therapeutic drug because: (i) it inhibits $T_{reg}$ suppressive functions and (ii) inhibit tumor cell expression of PD-L1, both of which enhances antitumor immune response. In addition, (iii) USP22i-S02 can directly inhibit tumor cell proliferation through USP22 suppression.

Usp22i-S02 In Vivo Inhibitor Experiments.

LLC1 cells were transplanted into 6-to-8-week-old C57BL/6 male mice. Subcutaneous injections were performed in the right flank of mice in a final volume of 100 μL using 1^6 cells per injection. The USP22i-S02 was injected intraperitoneally (i.p) at a concentration of 20 mg/kg/time, in 100 μL of oil, twice a day for 5 days beginning on the day of the LLC1 cells injection. Control animals received 100 μL of oil alone. Subcutaneous tumor diameters were measured daily with calipers until any tumor in the mouse cohort reached 2.5 cm in its largest diameter.

Example 2—USP22i-S02 Analogs

Biological screening confirmed that USP22i-S02 inhibited the expression of FoxP3 and PD-L1 expression in a USP22-dependent manner. The IC50 is about 6-7 uM. We further analysis of the structure-activity relationship (QSAR) between USP22i-S02 and USP22 deubiquitin inhibition (using MM/PBSA binding energy as an index), we showed that the compound S02 can be used as a lead compound in the E ring out of the five (A-E) (FIG. 1). In particular, modifications at the R position at A-Ring, or R1 and R2 at E-Ring are likely to improve its biological activity. Therefore, we used the SYBYL drug design software and generated a chemical library of 40400 derivatives (named as USP22-S02X) by modifying the A or/and E ring with 200 functional groups at the R or R1 or R2 or two of the three positions. Further virtual screening showed that 17 compounds potentially have improved USP22 suppressive activity (FIG. 1).

Figure 2:
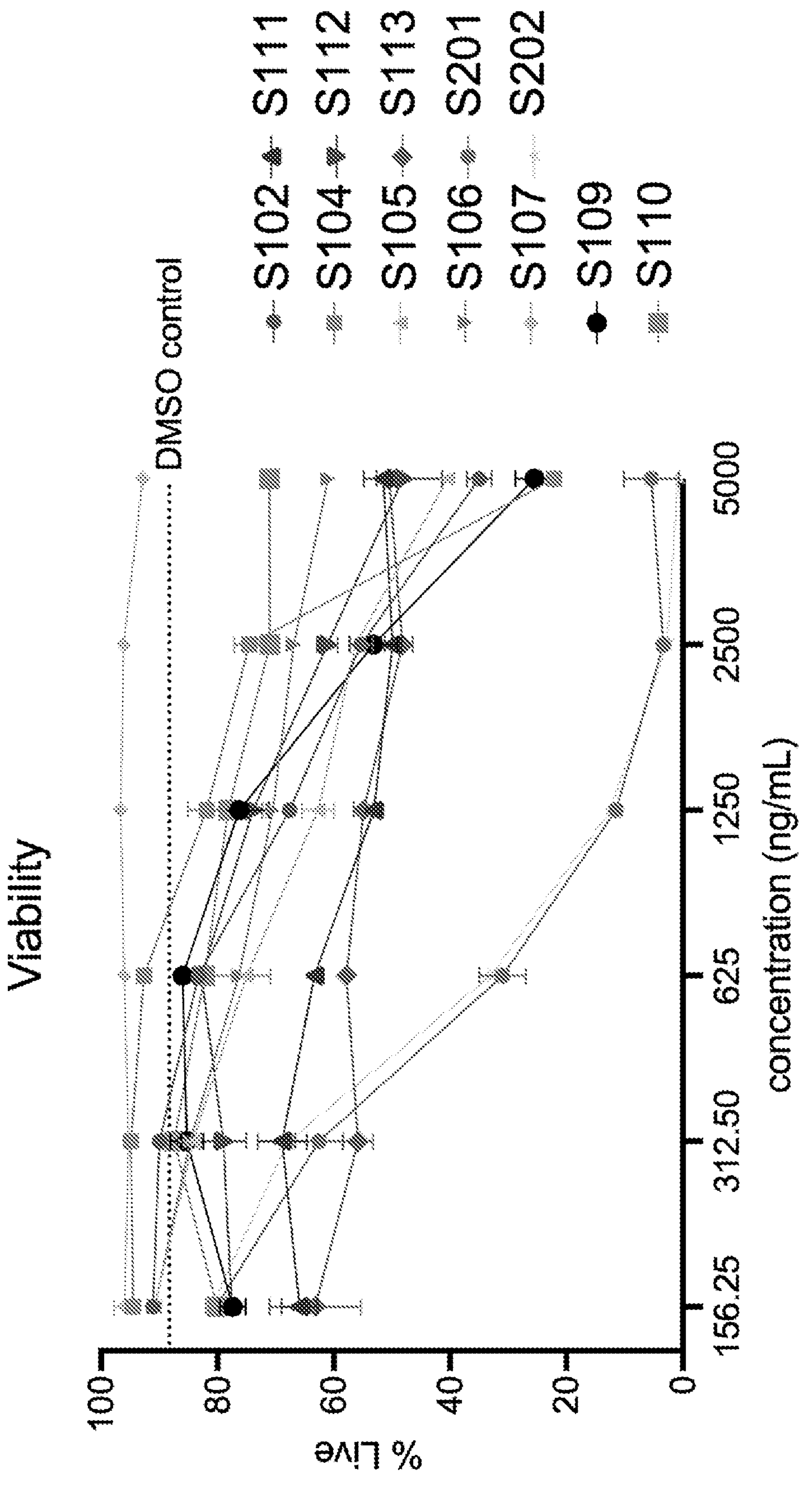
FIG. 2: Cytotoxicity of compounds from 156 ng/mL to 5 ug/mL concentration range in polarized CD4+ T-regulatory cells. Murine CD4+ T-cells were isolated and polarized in vitro to T-regulatory cells using 5 ng/mL IL-2, 2 μg/mL anti-IL-4, 2 μg/mL anti-IFNγ, and 1 ng/mL TGFβ. After 48 hours, the inhibitors were added to the cells. USP22i-s02 (not shown) does not show severe cytotoxicity compared to the DMSO control at 5 μg/mL. Inhibitors S105, 106, S107, S110, and S112 have the least cytotoxicity in vitro at 5 μg/mL concentration compared to the DMSO controls.

We then synthesized all 17 compounds and validated their cytotoxicity to regulatory T cells. To this end, mouse CD4 T cells were polarized to FoxP3 Tregs for two days, followed by treatment of the cells with each of the compounds at the doses upto 5 ug/ml. As shown in FIG. 2, S105, 106, S107, S110, and S112 have the least cytotoxicity, both S201 and 202 are extremely toxic to Tregs, and the compounds S102, 103, 104, 109, and 113 also showed modest toxicity to Tregs at higher concentrations. In addition, the rest of the compounds had poor solubility in DMSO, and were not further tested.

Figure 3:
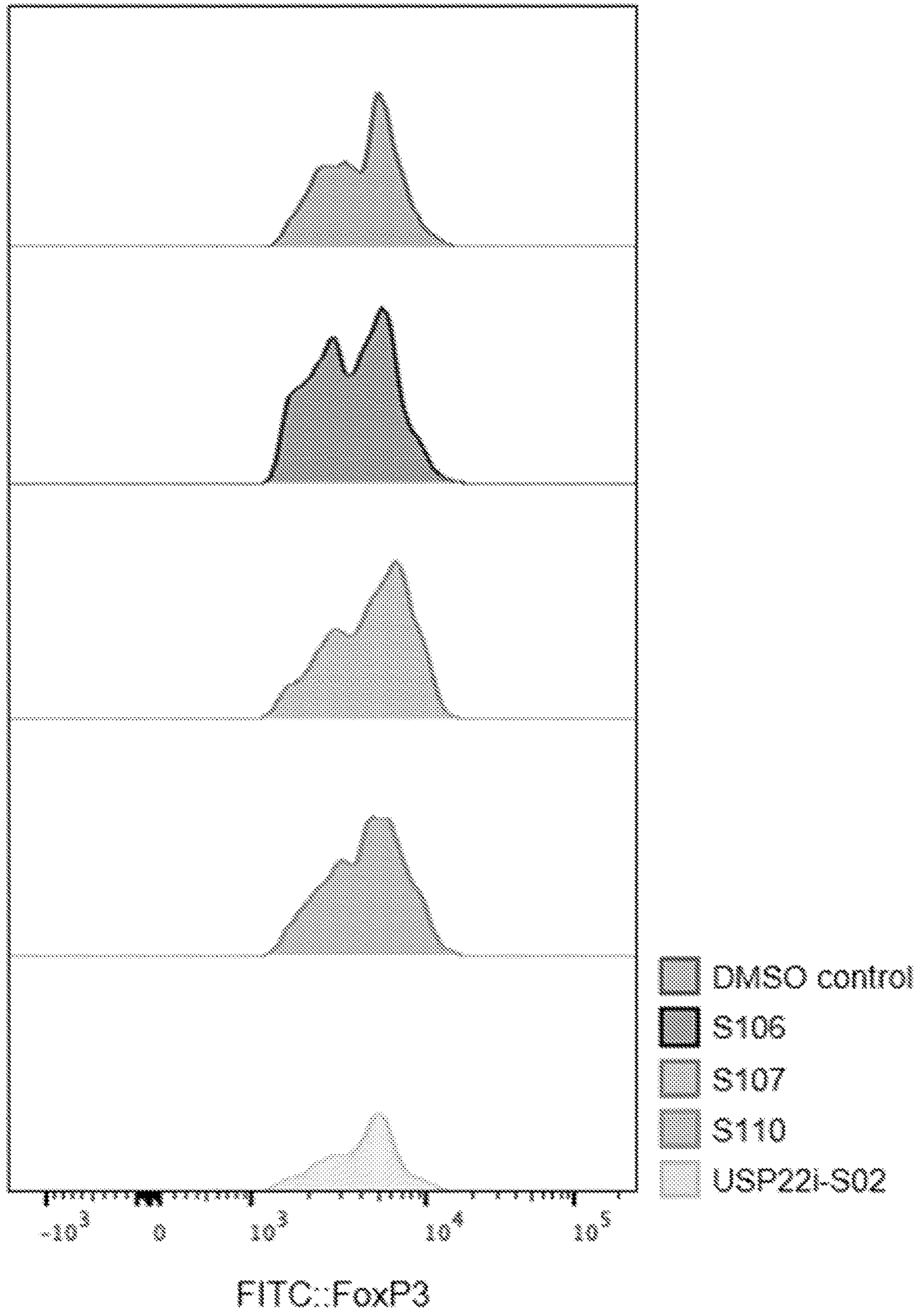
FIGS. 3 and 4: Change in FoxP3 expression in murine CD4+ natural T-regulatory cells. Murine lymphocytes were isolated from the spleens and lymph nodes and cultured with varying concentrations of inhibitor (0.25 μg/mL to 2 μg/mL) or DMSO, anti-CD3, anti-CD28, TGFβ, and IL-2. After two days, lymphocytes were analyzed by flow cytometry for FoxP3 expression in natural T-regulatory (nTregs) gated on CD3+CD4+CD25+FoxP3+.
Figure 4:
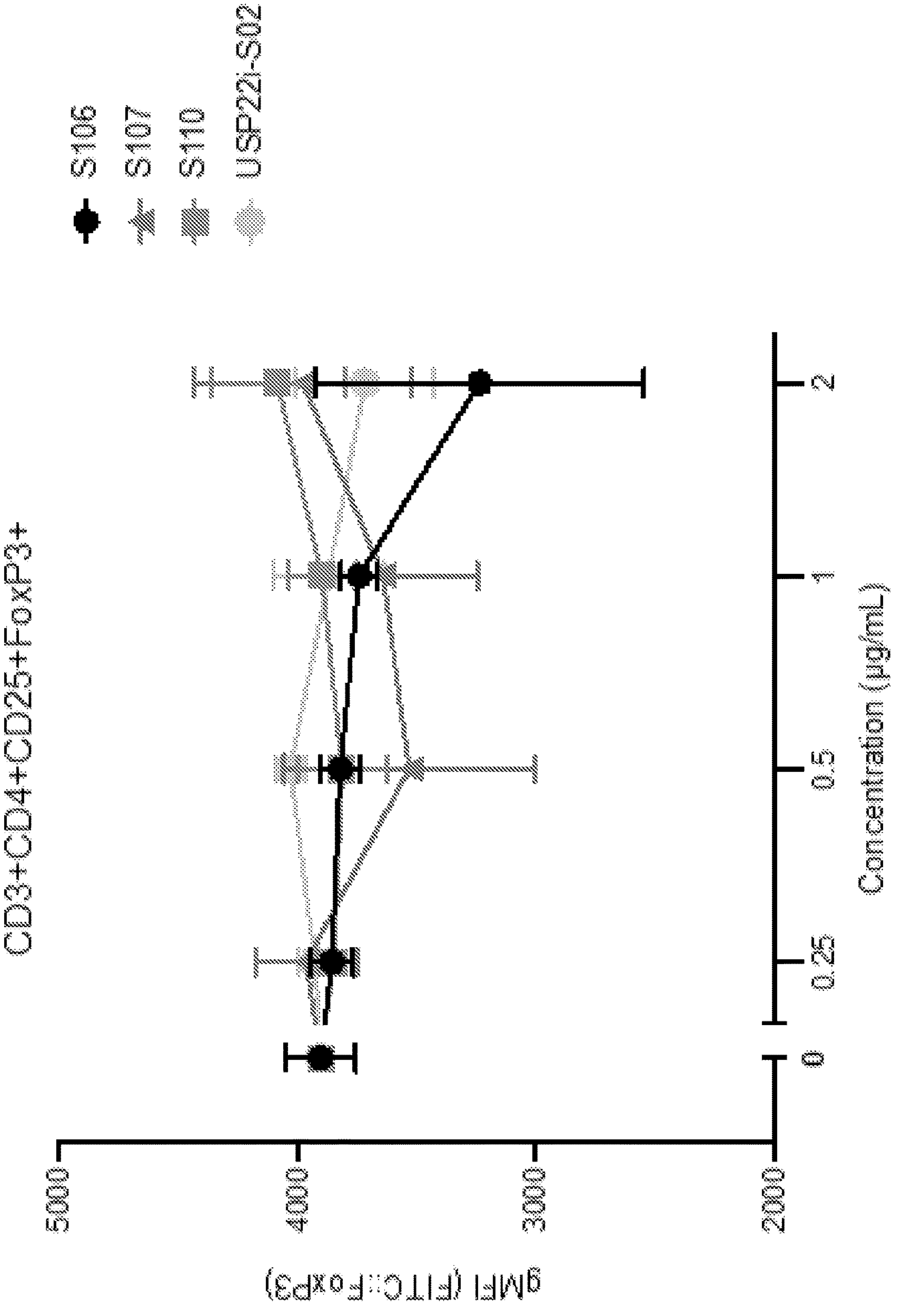

We then analyzed whether treatment of Tregs with the compounds S106, 107 and 110 inhibits USP22 activity in Tregs as measured by FoxP3 expression levels by flow cytometry. As shown in FIGS. 3-4, the compound S106 dose dependently reduced the USP22 substrate FoxP3 expression at concentration of 1-2 ug. In contrast, the lead compound S02 did not reduce the levels of FoxP3 at the same concentration, indicating that the compound S106 is a more potent USP22 inhibitor in Tregs.

Example 3—Design of USP22i-S02 Analogs by Virtual Screening

In order to optimize the virtual screening evaluation index system, this study analyzed the correlation between the computational simulation results of 25 emerging inhibitors and their corresponding biological activities. Studies have shown that in the virtual screening method, in addition to MM/PBSA (molecular mechanics/Poisson Boltzmann surface area) combines free energy as an important screening evaluation index, and the conformation of the compound in the molecular docking matches the active pocket, as well as the stability of the compound ligand during molecular dynamics simulation.

MM/PBSA binding free energy of compound S02 with USP22 is −297.43 kJ/mol, ranking the second among all 25 top compounds. However, although compound S01 ranked the best in MM/PBSA binding free energy (−342.23 kJ/mol), no biological activity in suppressing FOXP3 expression was detected [1]. Indeed, Compound S02 not only matches the USP22 catalytic activity pocket, but also maintains a relatively stable RMSD value with the USP22 protein structure during the 20 ns motion trajectory, indicating stable binding of compound S02 with USP22 during the simulation process (FIG. 4A). In contrast, the docking results show that the structure of compound S01 clearly extends beyond the catalytic pocket, and the RMSD is relatively unstable (FIG. 4B). Therefore, in addition to MM/PBSA binding free energy as an important screening evaluation index, we also included the conformational matching between the compound and the active pocket during molecular docking, and the stability of the compound ligand during molecular dynamics simulation to further optimize our virtual screening approaches.

Figure 9:
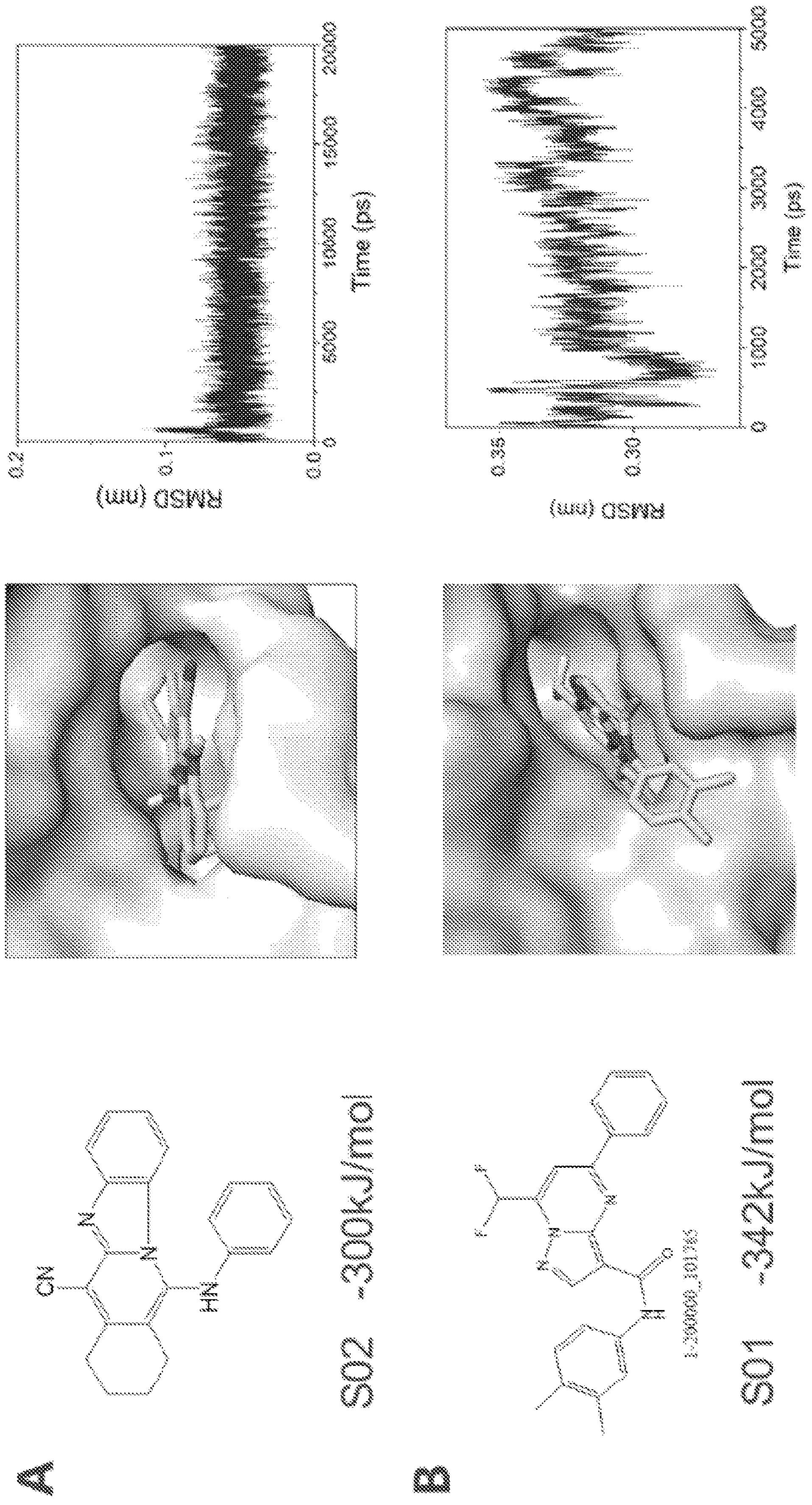
FIG. 9: Analysis of the stability and molecular dynamics of the USP22-S02 (A) and S01(B) binding with USP22 catalytic domain.
Figure 10:
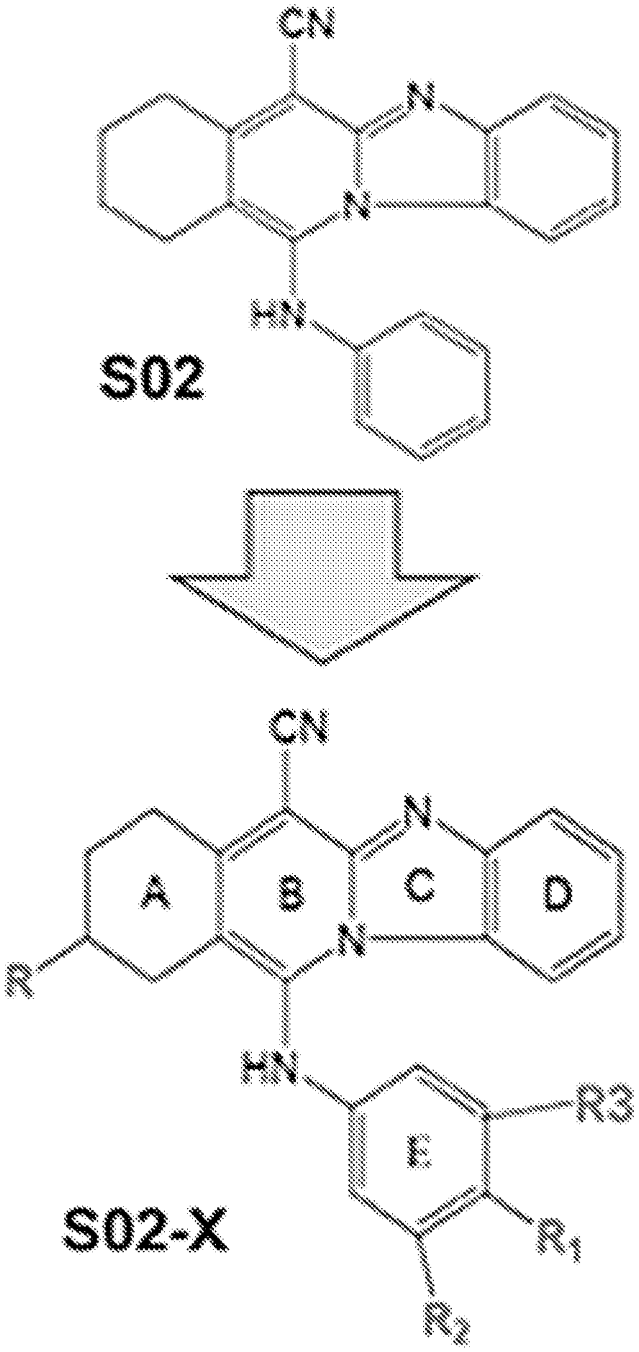
FIG. 10: USP22i-S02 is a lead compound to optimize its USP22 inhibitory activity. Analysis of the five-Ring geometry of USP22 identified the sites that can potentially modified at the position R1, R2 or R3 in ring E, as well as R in ring A, to improve its USP22 suppressive activity.
Figure 11:
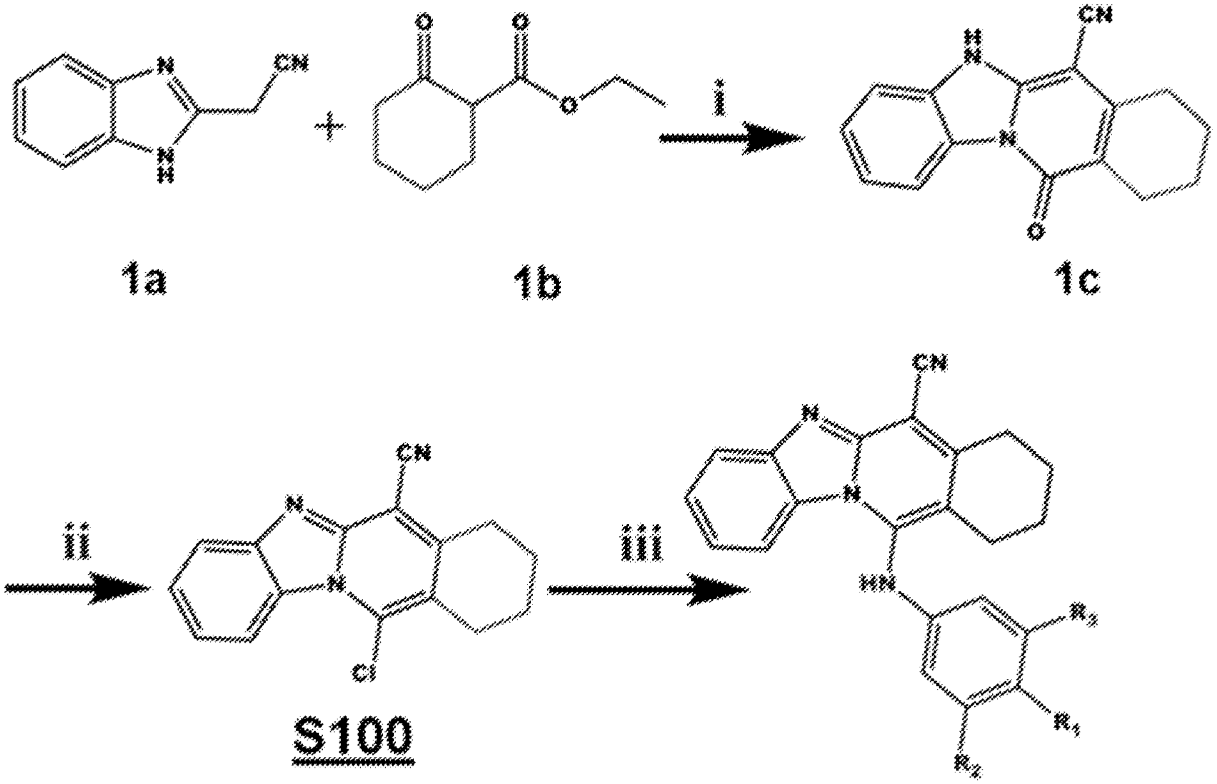
FIG. 11: (A) Three steps in USP22i-S02 analog synthesis. The synthetic strategy of USP22i-S02 at R1-3 in ring E. (B) Strategy for synthesis of USP22i-S02-S200, 201, and S202.
Figure 11:
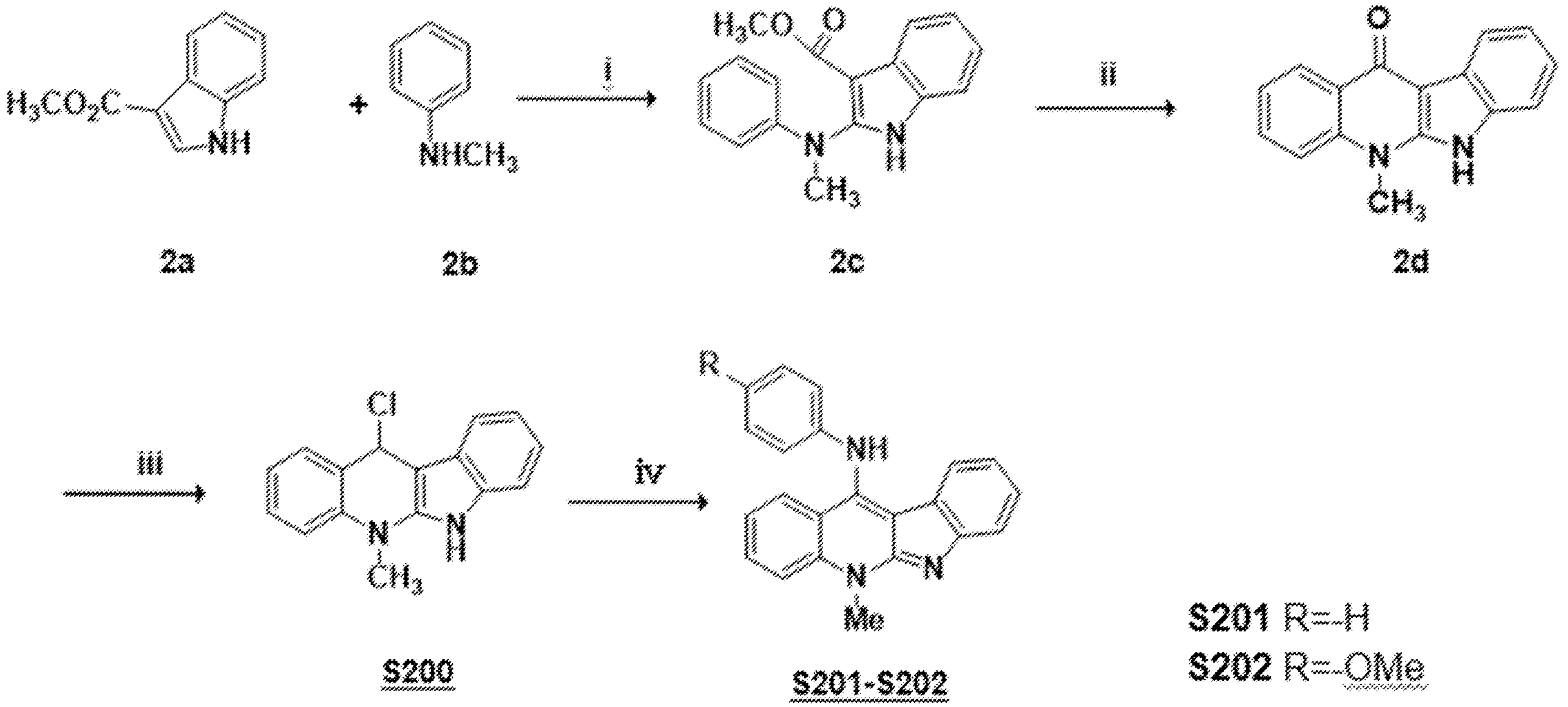

The geometric shape of compound 502, which contains five rings, was used as a reference for searching related analogues in the PubChem and SciFinder database. By analyzing the relationship among compound structure as in FIGS. 9A & B, we initially identified that optimizing the functional groups at positions $R_1$, $R_2$, with some positive addition from $R_3$, of ring E and the position R of ring A in S02 could enhance its biological activity (FIG. 10). Thus, we used Sybyl drug design software to generate a library of 40,400 derivatives by substituting 200 functional groups at positions R1 and R2 of ring E. Based on an optimized virtual screening evaluation index system, we selected the top 17 compounds with great potential to improve the inhibitory activity against USP22 compared to S02, all of which have been synthesized following the chemical reaction steps (FIG. 11).

Example 4—Synthetic Design

Our structure-based approach to drug design identified 12 S02 derivatives at the phenylaminobenzene ring. In order to add substituents or functional group fragments to the parent nucleus of benzimidazolium compounds, we first thought of constructing compounds such as S101 to facilitate the design of adding substituents and functional groups to the benzene ring. As shown in the flowchart (FIG. 11), we chose to utilize the 1a (1.0 equiv.) with the highest atomic efficiency. for the original substrate, and 1b (1.1 equiv.) as a substrate, dissolved in ammonium acetate (2.0 equiv.) (FIG. 11). Medium, solvent-free reaction at 150° C. for four h. Solvent-free is the use of ammonium acetate low melting point property, in the case of 150° C., the reaction substrate in the molten state of the reaction, can accelerate the reaction rate of the reaction, and after the reaction is completed, can use the dissolving properties of the final product, the use of acetonitrile washing final product, wash away the unreacted 1b and excess ammonium acetate and the resulting acetate. Intermediate products can be obtained at a high yield rate of 95% 1c. At the end of the reaction from 1a to S100, after the reaction drops to room temperature, the excess phosphorus trichloride in the system is steamed by rotary evaporator, and then the residual phosphorus trichloride in the system is quenched. Three times of extraction with ethyl acetate can yield a bright yellow solid S100 with a yield of 90% to 97%. HpPE data show that the product S100 (11-chloro-7, 8,9, 10-tetrahydrobenzo [4,5] imidazo [1,2-b]isoquinoline-6-carbonitrile) has a high purity. HPLC (5-100 MeOH-in30 min, t=21.928, S=92.20, 280 nm; t=21.936, S=89.37, 254 nm). After obtaining a very high purity of S100, we can react with aniline of different kinds of substituents, with SN2 as the reaction (Nucleophilic Substitution), and finally get the benzimidazole compounds S101-S113 (FIG. 11).

On the other hand, we searched for S02 (S101) analogues through the pubchem database and found that indole and quinoline compounds may also inhibit USP22 activity. Subsequently, unlike benzimidazoles, we have selected a structure of the indoline and quinoline compounds with the addition of the 7th position to the structure of the compounds containing methyl indolines (FIG. 11). Different types of aniline were selected as the reaction substrate, and the simple, convenient and efficient SN2 reaction was used as the reaction route to obtain indole and quinoline compounds that could be screened.

All reagents involved in the reaction are commercially purchased direct reagents from Sigma Aldrich (Shanghai) Trading Co., Ltd. (Aldrich), TCI, Enig Chemicals (Energy). And Bought with companies such as J&K Chemical Technology. All products are separated by column chromatography using newly made silicone columns. The Silica gel plate of model F-254 is used for thin layer chromatography (TLC) analysis, and the color development method is usually used: phosphor molybdenum acid color developer, ultraviolet lamp irradiation, iodine tank fumigation, alkaline potassium permanganate color developer, etc.

Intermediate product 1c synthesis Weigh methyl 2-oxycyclohexane carboxylate (6.3 mmol, 1.2equiv.), 2-cyanomethylbenzoimidazole (6.8 mmol, 1.1equiv.), ammonium acetate (12.6 mmol, 2.0 equiv), pour into a 50 mL round-bottom flask, heat 150° C. without solvent, return to room temperature after the reaction for 4 h, then wash with acetonitrile (3×50 mL), wash until the color disappears, dry off-white solid 1c (yield 96%).

Intermediate product S100 synthesis Weigh dried 1c off-white solid compound (6.3 mmol, 1.0 equiv.), $POCl_3$ (15equiv.); Put the 50 round bottom flask, reflux condenser tube, magnet into the oven at 120° C., after 2 h take out the rubber stopper, and press an argon balloon, after cooling, put the weighed compound into the round bottom flask, heat it to 120° C., and return. After 6 h of reaction, return to room temperature; Phosphorus trichloride was steamed off with a rotary evaporator, the concentration system was slowly added to sodium bicarbonate under an ice bath, the PH was adjusted to neutral and then extracted with ethyl acetate (3×20 mL), and then filtered to obtain a yellow-green powder solid S100 (yield of 98%).

General Procedure for the Synthesis of S200-202 (FIG. 11B)

General Procedure for the Synthesis of Intermediate 2c. 2a (1.0 equiv.) and N-chlorosuccinimide (NCS) (1.1 equiv.) were added to a 50 mL round-bottom flask and dissolved in 5 mL of dichloromethane (DCM) solvent. The solution was degassed under Ar or N2 for 2 minutes and then N,N-dimethylpiperazine (0.5 equiv.) was slowly added dropwise at ice-bath. The reaction was allowed to proceed for 2 hours and TLC was used to confirm the completion of the reaction. The mixture was then allowed to reach room temperature, and trifluoroacetic acid (0.125 equiv.) was dissolved in DCM and slowly added to the reaction mixture. Next, 2b (2.0 equiv.) was slowly added dropwise to the system. The reaction was allowed to proceed at room temperature for 3 hours, and TLC was used to confirm that 2b had completely reacted. The mixture was then transferred to an ice-bath, and a saturated solution of sodium bicarbonate (5 mL) was slowly added dropwise to adjust the pH to neutral. Ethyl acetate (3×20 mL) and water (3×200 mL) were then added for extraction, and the organic layer was collected. Anhydrous sodium sulfate was added to dry the organic layer, and the remaining ethyl acetate was removed by rotary evaporation. The crude product was purified by column chromatography using ethyl acetate and petroleum ether (ethyl acetate/petroleum ether=25%) as the eluent. The final product 2c was obtained in 85% yield.

General Procedure for the Synthesis of Intermediates 2d. 2c (1.0 equiv.) and diphenyl ether (10.0 equiv.) were placed in a 100 mL round-bottom flask and degassed under Ar or N2 for 2 minutes. The mixture was then refluxed using a reflux condenser at 150° C. for 6 hours. TLC was used to confirm the complete reaction of 2c. The mixture was cooled to room temperature, and then washed with ethyl ether (100 mL×3) to remove excess diphenyl ether. The remaining mixture was then concentrated by rotary evaporation to remove excess ethyl ether, and the resulting crude product was dried. The final product 2d was obtained in 91% yield.

General Procedure for the Synthesis of Intermediates S200. 2d (1.0 equiv.) and phosphorus oxychloride (5.0 equiv.) were placed in a 50 mL anhydrous round-bottom flask, and a solution was prepared by injecting 10 mL of toluene solvent. The mixture was heated to reflux at 135° C. After 6 hours, TLC was used to confirm the complete reaction of 2d. The mixture was cooled to room temperature, and then the toluene and phosphorus oxychloride were removed by rotary evaporation. The residue was then cooled in an ice bath, and 100 mL of saturated sodium bicarbonate solution was added to remove the remaining phosphorus oxychloride. The pH was adjusted to neutral, and then the mixture was extracted with ethyl acetate (3×20 mL) and water (3×200 mL). The organic layer was collected, and excess ethyl acetate was removed by rotary evaporation. Finally, column chromatography was performed with an eluent mixture of ethyl acetate and petroleum ether (ethyl acetate/petroleum ether ratio=25%). The resulting bright orange product S200 was obtained with a yield of 86%.

NMR spectrum of USP22i-S02-S200: 11-chloro-5-methyl-6,11-dihydro-5H-indolo[2,3-b]quinoline: orange solid, yield 86%. 1 H NMR (500 MHz, CDCl3) δ=8.44-8.47 (m, 2H), 7.80-7.84 (m, 1H), 7.73-7.77 (m, 2H), 7.57-7.61 (m, 1H), 7.51-7.55 (m, 1H), 4.36 (s, 3H).

General Procedure for the Synthesis of S201 and S202. General procedure for the reaction: Weigh out S200 orange solid (0.41 mmol, 1.0 equiv.) and aniline (2.0 equiv.) or p-anisidine (2.0 equiv.) and place them in a 50 mL round bottom flask. Prepare a solution by injecting 2 mL of DMF solvent through the needle and purge the flask with argon or nitrogen gas for 2 minutes. Seal the reaction flask with a septum and then heat it to 80° C. After a 4-hour reaction, check the completion of the reaction by TLC. After S200 has completely reacted, cool to room temperature, and then add ethyl acetate (3×20 mL) and water (3×200 mL) to remove DMF with water washing. Then, use a rotary evaporator to remove the remaining ethyl acetate. Finally, perform column chromatography separation using ethyl acetate and petroleum ether (ethyl acetate/petroleum ether=25%) as the eluent. The final concentrated products S201 (yield: 75%) and S202 (yield: 67%) are obtained.

NMR spectrum of USP22i-S02-S201: N5-methyl-N-phenyl-5H-indolo[2,3-b]quinolin-11-amine: light yellow solid, yield 78%. 1 H NMR (400 MHz, Choloroform-d) δ=8.11 (d, J=8.3 Hz, 1H), 7.42 (ddd, J=8.1, 7.3, 1.2 Hz, 1H), 7.35 (ddd, J=8.2, 5.9, 2.1 Hz, 1H), 7.28 (s, 1H), 7.25-7.29 (m, 2H), 7.07-6.90 (m, 5H), 4.33 (s, 3H).

NMR spectrum of USP22i-S02-S202: N,5-dimethyl-5H-indolo[2,3-b]quinolin-11-amine compound with anisole:

light yellow solid, yield 67%. 1 H NMR (500 MHz, CDCl3) δ=8.71 (d, J=10.0 Hz, 1H), 8.18-8.21 (m, 1H), 8.04-8.08 (m, 1H), 7.71 (t, J=20.0 Hz, 1H), 7.57-7.59 (m, 1H), 7.38-7.42 (m, 1H), 7.18-7.21 (m, 1H), 6.91-6.97 (m, 2H), 6.48-6.52 (m, 1H), 4.34 (s, 3H), 3.83 (s, 3H).

Example 5—Analysis of USP22i-S02 Analogs

Figure 12:
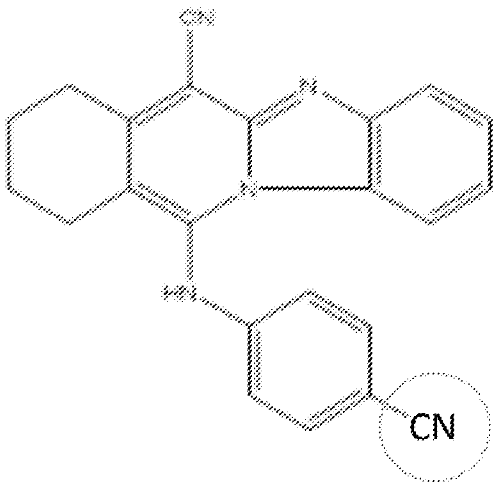
FIG. 12: USP22i-S02-S106 achieves the most potent USP22 inhibitory activity. (A) The chemical structure of S02-S106 11-((4-cyanophenyl)amino)-7,8,9,10-tetrahydrobenzo(4,5)imidazole[1,2-b]isoquinoline-6-carbonitrile, (B & C) The efficacy of USP22i-S02 analogs in inhibiting USP22 catalytic activity was determined in vitro. The representative data from a triplicate analysis of S02-S106 with S02 as a control are shown (B). The IC50 of USP22i-S02 analogs in suppressing USP22 in vitro catalytic activity are shown (C). NA, not available.
Figure 12:
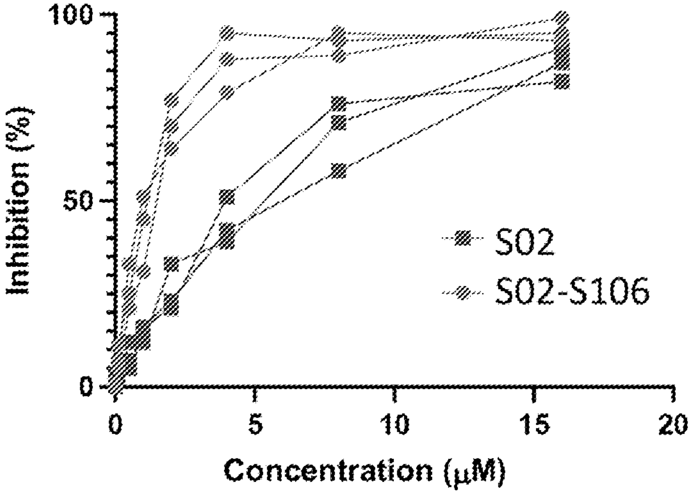

It has been suggested that in vitro purified USP22 protein lacks catalytic activity, because its catalytic pocket opens only when USP22 binds to SAGA complex proteins including Sgf11 and Sgf73 and Sus1 [2,3]. Indeed, we have generated the GST-USP22 fusion protein and demonstrated that the purified GST-USP22 inhibited Sirt1 poly-ubiquitination only when with a high concentration, indicating that the purified USP22 protein catalytic activity, while not totally dead, is largely impaired [4]. Interestingly, a recent study shows that re-construction of the yeast deubiquitination module of SAGA complex in vitro by incubation of the purified Ubp8, Sgf11 and Sgf73 1-105 and Sus1 proteins can inhibit the mono-ubiquitination of histone 2B (H2B-ub) [5]. We purchased human recombinant Sgf11 and Sgf73 1-105 and Sus1 proteins from R&D Systems Inc, and re-constructed the deubiquitination activity with our human GST-USP22. The USP22 customized deubiquitination was optimized and used for in vitro screening the activity of synthetic USP22i-s02 analogs with the USP22i-s02 as a control (FIG. 12). The IC50 of the lead compound USP22i-S02 is about 4.7 μM. In contrast, two of its analogs have a dramatic increased efficacy in suppressing USP22 activity: the S02-S106 (11-((4-cyanophenyl)amino)-7,8,9,10-tetrahydrobenzo(4,5)imidazole[1,2-b]isoquinoline-6-carbonitrile and S02-S113, (11-((4-aminomethyl)phenyl)amino)-7,8,9,10-tetrahydrobenzo(4,5)imidazole[1,2-b]isoquinoline-6-carbonitrile has the most potent efficacy of 0.6 μM and 0.3 μM, respectively. In addition, S02-S105 and S02-S107 also showed a slight improvement of USP22 inhibitory activity. Since S02-S113 is highly toxic, we then focused on evaluation of the S02-S106. Therefore, our studies demonstrated that addition of the cyano group at R1 position of E ring significantly improved USP22i-S02 inhibitory activity by at least 8 folds without increasing its toxicity.

Figure 13:
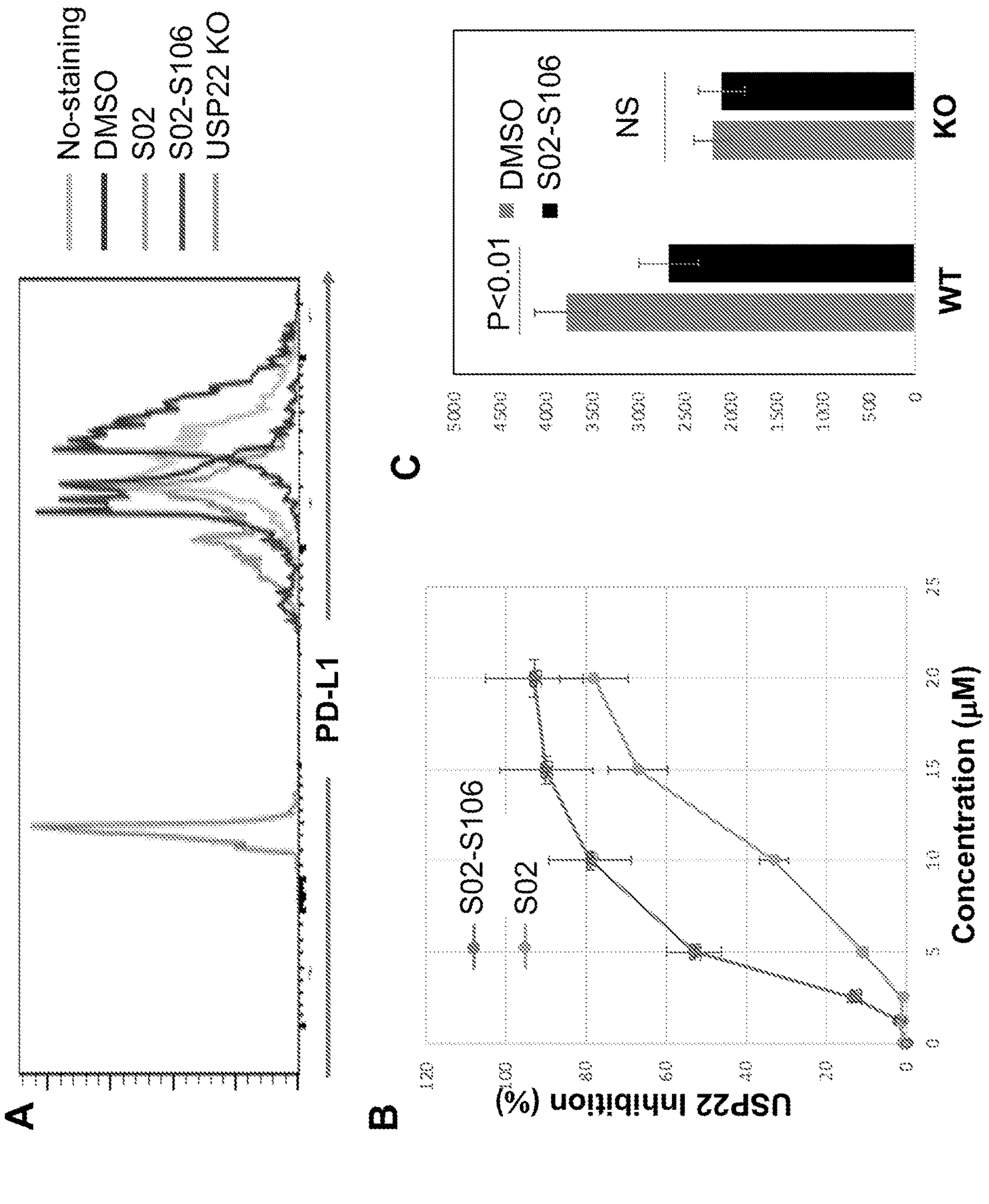
FIG. 13: The effects of USP22i-S02-S106 on suppression of PD-L1 expression on human lung adenocarcinoma cells. Human small cell lung adenocarcinoma A549 cells were treated with S02-S106 or its lead compound S02 for 48 hours. The expression levels of PD-L1 were determined by flow cytometry. (A) Representative flow data from A549 cells treated with 2 μM S02-S106 or with 15 μM S02 are shown. DMSO treated cells were used as an untreated control and USP22 CRISPR knockout A549 cells were used as a positive control. (B) The dose-dependent inhibition of PD-L1 expression in A549 cells by S02-S106 with USP22i-S02 as a control. Data were normalized with PD-L1 expression levels in USP22-KO cells as 100% of USP22 inhibition as shown in A. (C) Inhibition of PD-L1 expression in WT and USP22-null A549 cells by S02-S106.

We and others have demonstrated that the checkpoint receptor PD-L1 is a bona fide substrate of USP22 in cancer cells[6,7]. We then used PD-L1 expression level as a measurement to evaluate the inhibitory efficacy of USP22 by S02-S106. Since USP22 inhibition reduces PD-L1 in a cancer cell type-specific manner [7], we screened several cancer cell lines and discovered that USP22 genetic deletion in human lung adenocarcinoma resulted in a most dramatic PD-L1 reduction (FIG. 13A). Consistent with our results from in vitro USP22 deubiquitination assay, treatment of A549 cells with S02-S106 at achieved a 2 μM achieved a better efficacy than S02 at 15 μM in suppressing PD-L1 expression (FIG. 13A). Further dose-dependent analysis demonstrated that S02-S106 inhibited PD-L1 expression with an IC50 of about 3.2 μM. In contrast, the lead compound S02 inhibited PD-L1 expression with an IC50 of 13.7, indicating that addition of the cyano at the R1 position of E ring significantly improved the inhibitory efficacy in a cell-based study.

To determine the specificity of USP22i-S02-S106, we treated the WT and USP22-null lung cancer cells. Indeed, treatment of WT A549 cells with USP22i-S02-S106 dramatically inhibited PD-L1 expression to a level comparable to that of USP22-null A549 cells. Importantly, treatment of USP22-null A549 cells did not further reduce PD-L1 expression, clearly indicating that USP22i-S02-S106 inhibits PD-L1 expression in fully in a USP22-dependent manner.

Collectively, our current studies demonstrated that addition of the cyano at R1 position of E ring significantly improved the inhibitory efficacy by 4-8 folds without increasing the cytotoxicity. Therefore, the USP22i-S02-S106 is a highly specific and potent $2^{nd}$ generation USP22 inhibitor.

REFERENCES

[1] E. Montauti, S. E. Weinberg, P. Chu, S. Chaudhuri, N. L. Mani, R. Iyer, Y. Zhou, Y. Zhang, C. Liu, C. Xin, S. Gregory, J. Wei, Y. Zhang, W. Chen, Z. Sun, M. Yan, D. Fang, A deubiquitination module essential for T(reg) fitness in the tumor microenvironment, Sci Adv 8 (2022) eabo4116. 10.1126/sciadv.abo4116.

[2] N. L. Samara, A. B. Datta, C. E. Berndsen, X. Zhang, T. Yao, R. E. Cohen, C. Wolberger, Structural insights into the assembly and function of the SAGA deubiquitinating module, Science 328 (2010) 1025-1029. 10.1126/science.1190049.

[3] A. Kohler, E. Zimmerman, M. Schneider, E. Hurt, N. Zheng, Structural basis for assembly and activation of the heterotetrameric SAGA histone H2B deubiquitinase module, Cell 141 (2010) 606-617. 10.1016/j.cell.2010.04.026.

[4] Z. Lin, H. Yang, Q. Kong, J. Li, S.-M. Lee, B. Gao, H. Dong, J. Wei, J. Song, D. D. Zhang, D. Fang, USP22 Antagonizes p53 Transcriptional Activation by Deubiquitinating Sirt1 to Suppress Cell Apoptosis and Is Required for Mouse Embryonic Development, Molecular Cell 46 (2012) 484-494. 10.1016/j.molcel.2012.03.024.

[5] M. Morgan, T. Ikenoue, H. Suga, C. Wolberger, Potent macrocycle inhibitors of the human SAGA deubiquitinating module, Cell Chem Biol 29 (2022) 544-554 e544. 10.1016/j.chembiol.2021.12.004.

[6] X. Huang, Q. Zhang, Y. Lou, J. Wang, X. Zhao, L. Wang, X. Zhang, S. Li, Y. Zhao, Q. Chen, T. Liang, X. Bai, USP22 Deubiquitinates CD274 to Suppress Anticancer Immunity, Cancer Immunol Res 7 (2019) 1580-1590. 10.1158/2326-6066.CIR-18-0910.

[7] S. Gregory, Y. Xu, P. Xie, J. Fan, B. Gao, N. Mani, R. Iyer, A. Tang, J. Wei, S. M. Chaudhuri, S. Wang, H. Liu, B. Zhang, D. Fang, The ubiquitin-specific peptidase 22 is a deubiquitinase of CD73 in breast cancer cells, Am J Cancer Res 12 (2022) 5564-5575.

The invention claimed is:

1. A compound of formula (Ia)

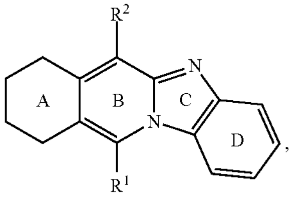

or a pharmaceutically acceptable salt thereof, wherein $R^2$ is selected from cyano and $R^1$ is —NH-phenyl, the phenyl substituted with halo, —CN, alkyl, alkoxy,—$NO_2$, amino, or —COOH and wherein the alkyl is optionally substituted with a halo or amino, or halo or wherein $R^2$ is selected from alkyl and $R^1$ is —NH-phenyl, the phenyl optionally substituted with halo, —CN, alkyl, alkoxy, —$NO_2$, amino, and —COOH and wherein the alkyl is optionally substituted with a halo or amino, or halo.

2. The compound of claim 1 having the formula

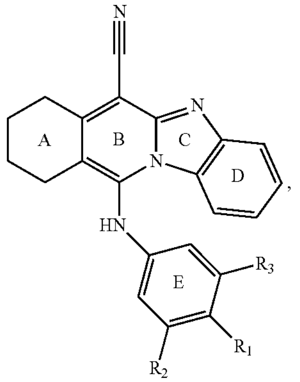

or a pharmaceutically acceptable salt thereof, wherein $R_1$, $R_2$, and $R_3$ are independently selected from hydrogen, halo, —CN, alkyl, alkoxy, —$NO_2$, amino, and —COOH, wherein the alkyl is optionally substituted with a halo or amino, and wherein $R_1$, $R_2$, and $R_3$ are not each hydrogen.

3. The compound of claim 1, wherein the compound is selected from

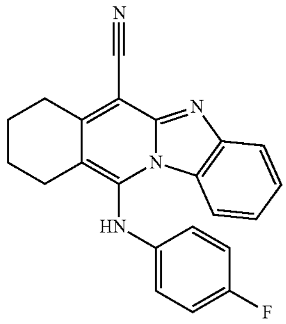

,

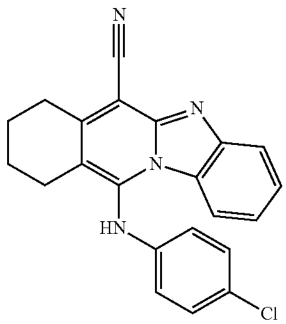

,

-continued
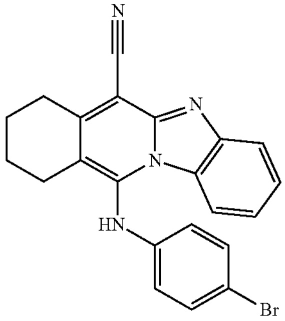
,
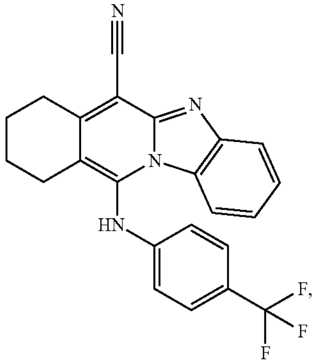
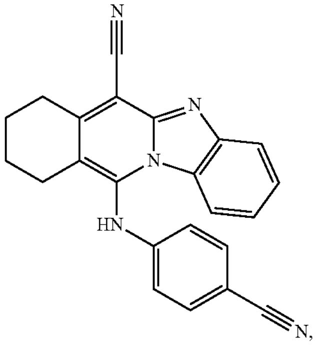
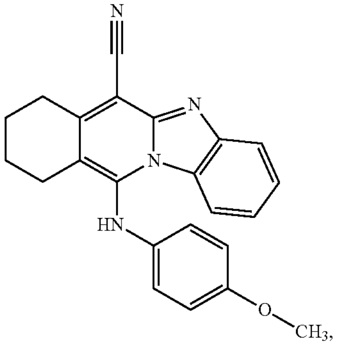
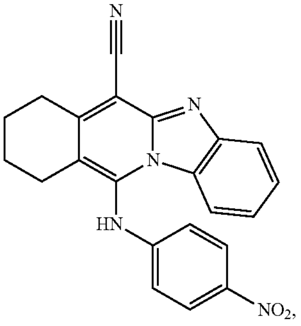
-continued
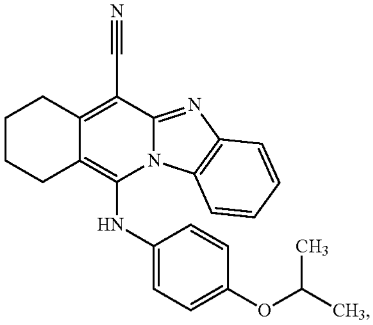
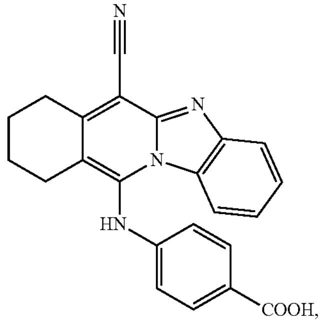
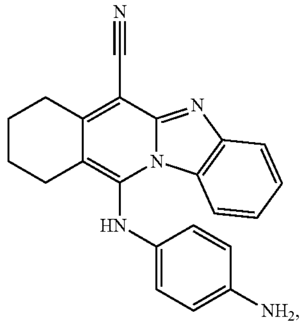
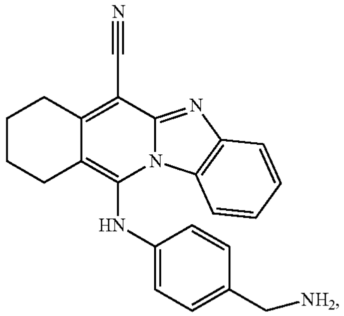
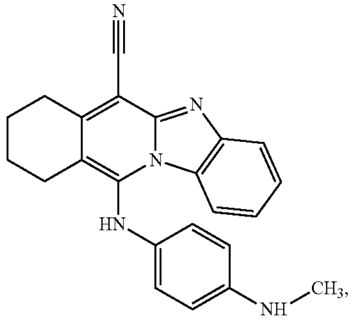

-continued

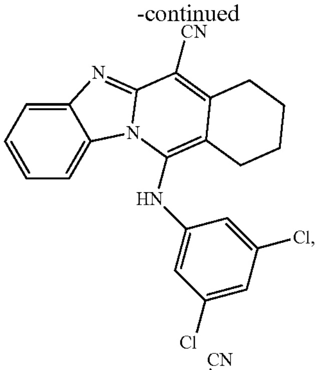

and

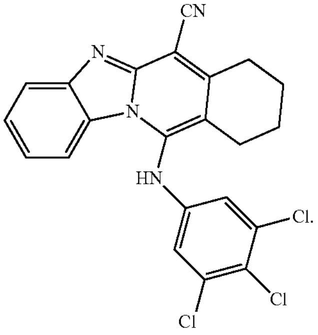

4. The compound of claim 1, wherein the compound is

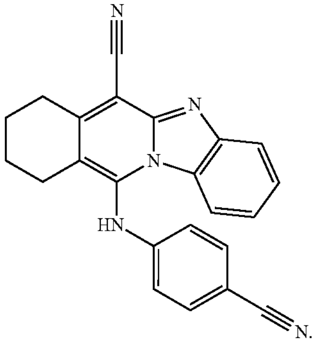 [SMILES: N#Cc1ccc(Nc2c3c(c(C#N)c4nc5ccccc5n24)CCCC3)cc1]

5. A pharmaceutical composition comprising the compound of claim 1 and a pharmaceutically acceptable carrier, excipient, or diluent.

6. The pharmaceutical composition of claim 5, wherein the composition comprises an effective amount of the compound for inhibiting biological activity of USP22 when administered to a subject in need thereof.

7. The pharmaceutical composition of claim 5, wherein the composition comprises an effective amount of the compound for suppressing Treg cell activity in a subject in need thereof.

8. The pharmaceutical composition of claim 5, wherein the composition comprises an effective amount of the compound for inhibiting ubiquitin specific peptidase activity (E.C. 3.4.19.12) of USP22 in a subject in need thereof.

9. A method of treating a subject in need of treatment for a disease or disorder associated with ubiquitin specific peptidase 22 (USP22) activity, the method comprising administering to the subject an effective amount of the pharmaceutical composition of claim 5, wherein the disease or disorder is a cancer selected from the group consisting of lung cancer, gastric carcinoma, pancreatic cancer, melanoma, lymphoma, colon cancer, breast cancer, ovarian cancer, bladder cancer, prostate cancer, glioma, mesothelioma, neuroblastoma, mantle cell lymphoma, and acute myeloid leukemia.

10. The method of claim 9, wherein the disease or disorder is lung cancer.

11. The method of claim 9, wherein the disease or disorder is melanoma.

12. A method for inhibiting ubiquitin specific peptidase activity (E.C. 3.4.19.12) of USP22 in a subject in need thereof, the method comprising administering to the subject an effective amount of the pharmaceutical composition of claim 5.

* * * * *